US010543210B2

(12) United States Patent
Wise et al.

(10) Patent No.: US 10,543,210 B2
(45) Date of Patent: Jan. 28, 2020

(54) INHIBITORS OF MULTIDRUG RESISTANCE TRANSPORTER P-GLYCOPROTEIN

(71) Applicant: Southern Methodist University, Dallas, TX (US)

(72) Inventors: John G. Wise, Dallas, TX (US); Pia D. Vogel, Dallas, TX (US); Alexander R. Lippert, Dallas, TX (US); Amila K. Nanyakkara, Dallas, TX (US); Maha A. Aljowni, Dallas, TX (US)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 16/366,674

(22) Filed: Mar. 27, 2019

(65) Prior Publication Data

US 2019/0216811 A1    Jul. 18, 2019

Related U.S. Application Data

(63) Continuation of application No. 15/911,441, filed on Mar. 5, 2018, now Pat. No. 10,292,982, which is a continuation-in-part of application No. 15/406,036, filed on Jan. 13, 2017, now Pat. No. 10,172,855, which is a continuation of application No. 14/598,022, filed on Jan. 15, 2015, now Pat. No. 9,561,227.

(60) Provisional application No. 61/927,767, filed on Jan. 15, 2014.

(51) Int. Cl.
| A61K 31/5025 | (2006.01) |
| A61K 31/4525 | (2006.01) |
| A61K 31/4196 | (2006.01) |
| A61K 31/353 | (2006.01) |
| A61P 35/00 | (2006.01) |
| A61K 45/06 | (2006.01) |

(52) U.S. Cl.
CPC ........ A61K 31/5025 (2013.01); A61K 31/353 (2013.01); A61K 31/4196 (2013.01); A61K 31/4525 (2013.01); A61P 35/00 (2018.01); A61K 45/06 (2013.01)

(58) Field of Classification Search
CPC . A61K 31/5025; A61K 31/352; A61K 31/353
See application file for complete search history.

(56) References Cited

U.S. PATENT DOCUMENTS

| 5,763,443 A | 6/1998 | Medlen et al. |
| 5,994,088 A | 11/1999 | Mechetner et al. |
| 6,365,357 B1 | 4/2002 | Mechetner et al. |
| 6,630,327 B1 | 10/2003 | Mechetner et al. |
| 7,144,704 B2 | 12/2006 | Mechetner et al. |
| 7,214,664 B2 | 5/2007 | Mitra et al. |
| 8,626,452 B2 | 1/2014 | Urry et al. |
| 9,561,227 B2 | 2/2017 | Wise et al. |
| 10,172,855 B2 | 1/2019 | Wise et al. |
| 10,292,982 B2 * | 5/2019 | Wise ................. A61K 31/4525 |
| 2009/0163545 A1 | 6/2009 | Goldfarb |
| 2010/0068786 A1 | 3/2010 | Chmielewski et al. |

FOREIGN PATENT DOCUMENTS

WO    2005100336 A1    10/2005

OTHER PUBLICATIONS

Barile, F.A., et al., "Acute cytotoxicity testing with cultured human lung and dermal cells," In vitro cellular & developmental biology, Animal, Sep. 1998, vol. 34, No. 8, pp. 631-635.
Brewer, F.K., et al., "In Silico Screening for Inhibitors of P-Glycoprotein that Target the Nucleotide Binding Domains," Molecular Pharmacology, vol. 86:6, Dec. 2014, pp. 716-726.
Chiang, C.C., et al., "Synthesis and HIV-1 Integrase Inhibition of Novel Bis- or Tetra-Coumarin Analogues," Chemical and Pharmaceutical Bulletin, vol. 55:12, Dec. 2007, pp. 1740-1743.
Li, Bo-Jian., et al., "QSAR Studies of 3,3'(Substituted-Benzylidene)-Bis-4-Hydroxycoumarin, Potential HIV-1 Integrase Inhibitor," Journal of the Chinese Chemical Society, vol. 57:4A, Aug. 2010, pp. 742-749.
Yang, A., et al., "Subacute Cytotoxicity Testing with Cultured Human Lung Cells," Toxicology in Vitro, vol. 16:1, Feb. 2002, pp. 33-39.
Yusa, Keisuke, et al., "Reversal Mechanism of Multidrug Resistance by Verapamil: Direct Binding of Verapamil to P-Glycoprotein on Specific Sites and Transport of Verapamil Outward across the Plasma Membrane of K562/ADM Cells," Cancer Research, vol. 49, Sep. 15, 1989, pp. 5002-5006.

* cited by examiner

*Primary Examiner* — Pancham Bakshi
(74) *Attorney, Agent, or Firm* — Edwin S. Flores; Chalker Flores, LLP

(57) ABSTRACT

The present disclosure provides a method of treating a subject that is resistant to one or more drugs by identifying a subject having one or more drug resistant cells; administering to the subject a pharmaceutically effective amount of an inhibitor compound, and contacting one or more drug resistant cells with the inhibitor compound to reduce the export of the inhibitor compound from the one or more drug resistant tumor cells and to block the transport of drug(s) from the one or more drug resistant cells.

4 Claims, 12 Drawing Sheets

INHIBITORS OF MULTIDRUG RESISTANCE TRANSPORTER P-GLYCOPROTEIN

CROSS-REFERENCE TO RELATED APPLICATIONS

This application claims priority to and is a continuation of U.S. patent application Ser. No. 15/911,441 filed on Mar. 5, 2018 and entitled "Inhibitors of Multidrug Resistance Transporter P-Glycoprotein," which is a continuation-in-part application of U.S. patent application Ser. No. 15/406,036 filed on Jan. 13, 2017 and entitled "Inhibitors of Multidrug Resistance Transporter P-Glycoprotein," which is a continuation of U.S. patent application Ser. No. 14/598,022 filed on Jan. 15, 2015 and entitled "Inhibitors of Multidrug Resistance Transporter P-Glycoprotein," which is a non-provisional application of U.S. Provisional Patent Application No. 61/927,767, filed Jan. 15, 2014, the contents of which are incorporated by reference in their entirety.

This application is also related to U.S. patent application Ser. No. 16/204,582 filed on Nov. 29, 2018 and entitled "Inhibitors of Multidrug Resistance Transporter P-Glycoprotein."

STATEMENT OF FEDERALLY FUNDED RESEARCH

This invention was made with government support under GM094771 awarded by the National Institutes of Health. The government has certain rights in the invention.

TECHNICAL FIELD OF THE INVENTION

The present invention relates in general to the field of chemotherapy, and more particularly, to the treatment of chemotherapy-resistant cancers, primary cancers and cancer stem cells, and in the field of modifying the blood brain barrier.

BACKGROUND OF THE INVENTION

Without limiting the scope of the invention, its background is described in connection with P-glycoprotein.

A fundamental characteristic of cancerous cells that normal cells lack is the ability of the cancerous cells to sustain chronic proliferation. Uncontrolled proliferation of cells in the body often creates a serious pathological state that requires medical intervention. The use of cancer chemotherapy began in 1948 when Sidney Farber reported that treating patients with a folate-dependent leukemia with an anti-folate chemotherapy could lead to temporary remissions in several children. Unfortunately, the toxic side effects of these chemotherapeutic agents prohibited extended therapy at that time. Within 25 years, combinations of different chemotherapeutics, tailored to specific cancers, had become routine. The most successful contemporary treatments for serious cancers often include localized treatment via surgical or radiation techniques when possible, followed by systemic chemotherapies. These chemotherapies often involve the parenteral administration of very cytotoxic compounds in attempts to eliminate proliferating cancer cells that remain in the body, while trying to not affect normal cells to the same degree.

U.S. Pat. No. 7,214,664, entitled "Peptidyl prodrugs that resist P-glycoprotein mediated drug efflux" discloses dipeptide, tripeptide, and tetrapeptide ester derivatives of bioactive agents that are substrates effluxed by the P-glycoprotein transporter. The derivatives are said to be useful in treating the same condition as the bioactive agent and a method for preparing a bioactive agent for targeted delivery by nutrient or peptide transporters comprising linking the agent to one or more groups of the formula —X—$Y_n$—$Z_{n'}$—$Z'_{n''}$—R; wherein each X, Y, Z, and Z' is independently Met, Val, Thr, Tyr, Trp, Ser, Ala or Gly; R is independently H or an amino-protecting group; n=1, and each, n', or n" is independently 0 or 1.

U.S. Pat. Nos. 7,144,704; 6,630,327; 6,365,357; and 5,994,088, related to methods and reagents for preparing and using immunological agents specific for P-glycoprotein are directed to immunological reagents and methods specific for a mammalian, transmembrane P-glycoprotein, which is said to be a non-specific efflux pump activity, and is clinically-important in multidrug resistance in cancer patients undergoing chemotherapy. They disclose methods for developing and using immunological reagents specific for certain mutant forms of P-glycoprotein and for wild-type P-glycoprotein in a conformation associated with substrate binding, or in the presence of ATP depleting agents, provide improved methods for identifying and characterizing anti-cancer compounds.

U.S. Pat. No. 5,763,443, entitled "MDR resistance treatment and novel pharmaceutically active riminophenazines" and discloses the use of riminophenazines in the treatment of a patient who has built up, or could build up, resistance to a therapeutically active substance, such as a patient requiring treatment for cancer, and includes novel riminophenazines, their preparation, and compositions containing them.

United States Patent Application Publication No. 2010/0068786, entitled "Methods and compositions for reversing P-glycoprotein medicated drug resistance," discloses a method for inhibiting therapeutic drug resistance within a cell over-expressing a membrane protein is provided, wherein the method comprises synthesizing a dimeric prodrug inhibitor of a monomeric therapeutic agent; administering the dimeric prodrug inhibitor to the membrane protein together with the monomeric therapeutic agent; and occupying at least one substrate binding site of the membrane protein with the synthesized dimeric prodrug to allow the monomeric therapeutic agent to accumulate within the cell. The dimeric prodrug inhibitor contains a crosslinking agent that is adapted to breakdown under reducing conditions within the cytosol of the cell to cause the dimeric prodrug to revert back to a form equivalent to the monomeric therapeutic agent.

Multidrug resistance is a significant problem in the pharmaceutical industry, and may be achieved by the activation of cellular membrane transporters. Drugs and certain proteins are transported across the membranes by energy-activated pumps where the outer membrane component of these pumps is a channel that opens from a sealed resting state during the transport process. For example, exporter proteins confer drug resistance by pumping the drug out of the cell before the drug can function or exert its intended effect (e.g., kill a cancer cell). Classical inhibitors of the exporter proteins are bulky hydrophobic molecules that overload the capacity of the hydrolysis of two ATP molecules to expel the drug by disruption of the hydrophobic associations, but these inhibitors lack specificity and are associated with significant side effects, disrupting important functions in tissues throughout the body.

U.S. Pat. No. 8,626,452, entitled "Compositions and methods for optimizing drug hydrophobicity and drug delivery to cells," discloses methods to determine drug hydrophobicity and to quantify changes in drug hydrophobicity that optimize drug function by means of differential scanning calorimetry of an endothermic phase transition of a base protein-based polymer, specifically of an elastic-contractile model protein, to which is attached to the drug to be evaluated for its hydrophobicity in terms of the change in Gibbs free energy for hydrophobic association have been developed. Also described is the preparation of nanoparticles comprised of protein-based polymers, specifically of elastic-contractile model proteins, designed for the binding and desired release rate of a specific drug or class of drugs. Further described is a means of targeting the drug-laden nanoparticle to a cell by means of decorating the nanoparticle surface with a molecular entity that selectively binds to the diseased cell or disease causing organism, e.g., by decorating the drug-laden nanoparticle surface with synthetic antigen-binding fragment to an up-regulated receptor characteristic of the diseased cell.

SUMMARY OF THE INVENTION

The present disclosure provides a method of treating a subject having a cancer that is resistant to one or more chemotherapeutic drugs by identifying a subject having one or more drug resistant cancer cells; administering to the subject a pharmaceutically effective amount of an inhibitor compound having one of the following structural formulas:

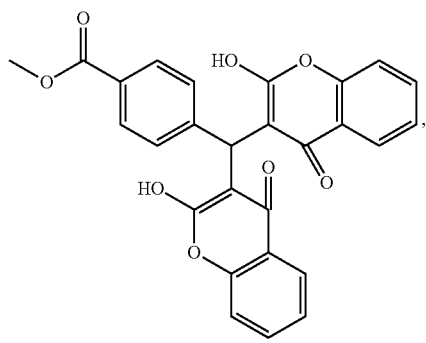

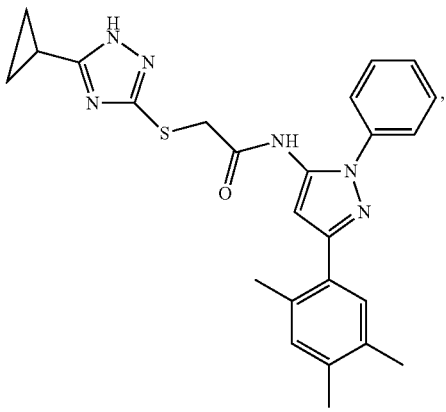

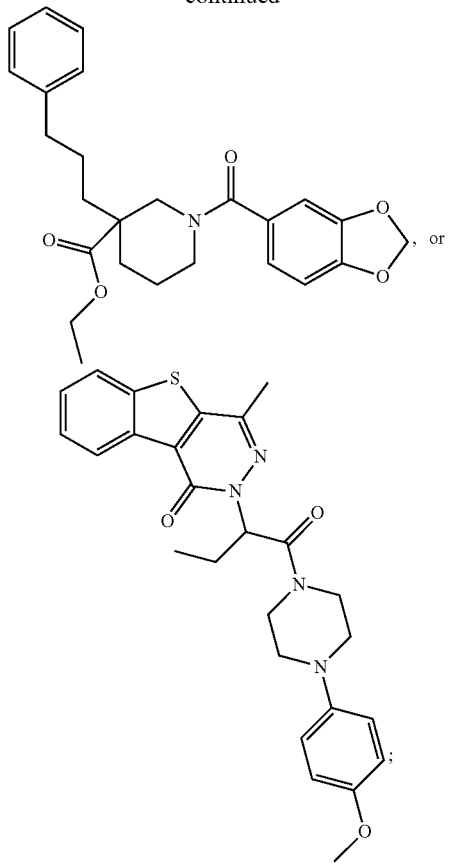

and contacting one or more drug resistant cancer cells with the inhibitor compound to reduce the drug resistance of the cancer cells. In one aspect, the inhibitor compound can reduce the export of the inhibitor compound from the one or more drug resistant tumor cells and/or block the transport of chemotherapeutic drug(s) from the one or more drug resistant cancer cells. In one aspect, the inhibitor compound interacts with an exporter protein. In another aspect, inhibitor compound is a P-glycoprotein inhibitor. In another aspect, the inhibitor compound interacts with drug-toxin pumping structures of a P-glycoprotein. In another aspect, the inhibitor compound interacts with ATP binding domain (s) of a P-glycoprotein and the inhibitor compound does not bind to drug binding site(s) on the P-glycoprotein. In another aspect, the inhibitor compound is minimally transported by a P-glycoprotein. In another aspect, the one or more drug resistant cancer cells are one or more multidrug resistant tumor cells. In another aspect, the one or more drug resistant cancer cells are lymphoma, leukemia, cancer stem cells, nonsmall-cell lung cancer, liver cancer, encephaloma, leukocythemia, carcinoma of prostate, intestine cancer, myeloma tumor, lymphoma, breast carcinoma, ovarian cancer, gastric cancer, small cell lung cancer, esophageal carcinoma, esophageal carcinoma, and sarcoma. In another aspect, further comprises the step of administering one or more chemotherapeutic agents to the subject.

The present disclosure provides a method of sensitization and re-sensitization of a cancer cell to a chemotherapeutic by identifying a subject having one or more cancer cells in need of sensitization and re-sensitization to one or more chemotherapeutics; administering to the subject a pharmaceutically effective amount of an inhibitor compound having one of the following structural formulas:

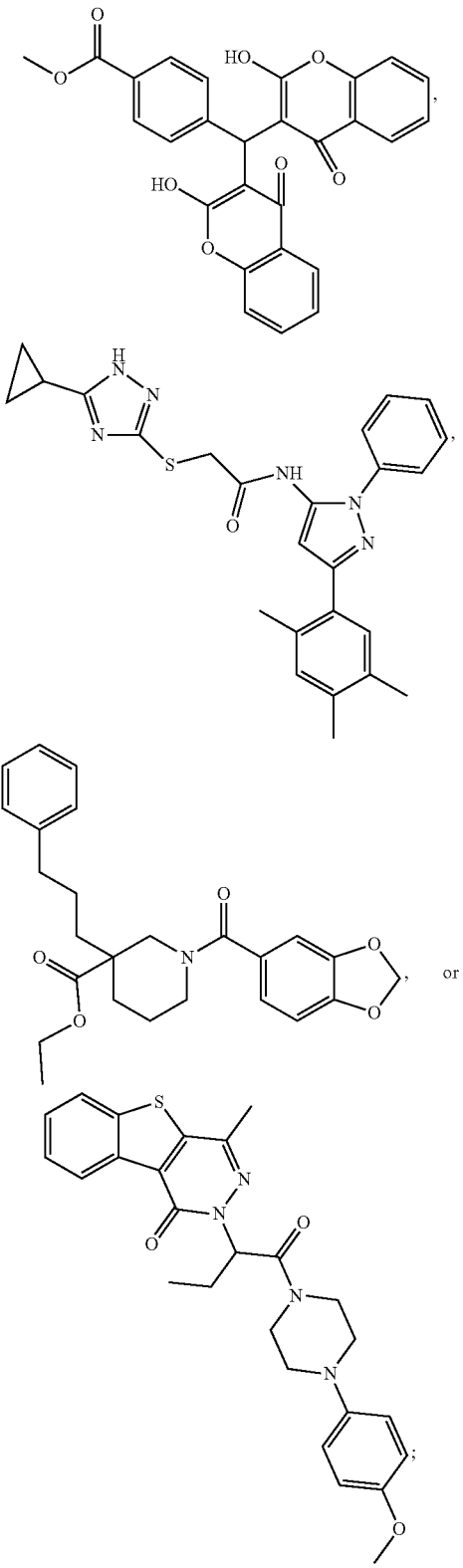

and contacting one or more cancer cells with the inhibitor compound to reduce the export of the inhibitor compound from the one or more cancer cells and to block the transport of the one or more chemotherapeutic drug(s) from the one or more cancer cells to sensitization or re-sensitization of the one or more cancer cells to the one or more chemotherapeutic drug(s). In one aspect, the inhibitor compound interacts with an exporter protein. In another aspect, inhibitor compound is a P-glycoprotein inhibitor. In another aspect, the inhibitor compound interacts with drug-toxin pumping structures of a P-glycoprotein. In another aspect, the inhibitor compound interacts with ATP binding domain(s) of a P-glycoprotein and the inhibitor compound does not bind to drug binding site(s) on the P-glycoprotein. In another aspect, the inhibitor compound is minimally transported by a P-glycoprotein. In another aspect, the one or more drug resistant cancer cells are one or more multidrug resistant tumor cells. In another aspect, the one or more drug resistant cancer cells are lymphoma, leukemia, cancer stem cells, nonsmall-cell lung cancer, liver cancer, encephaloma, leukocythemia, carcinoma of prostate, intestine cancer, myeloma tumor, lymphoma, breast carcinoma, ovarian cancer, gastric cancer, small cell lung cancer, esophageal carcinoma, esophageal carcinoma, and sarcoma. In another aspect, further comprises the step of administering one or more chemotherapeutic agents to the subject.

The present disclosure also provides a method of increasing an efficacy of one or more chemotherapeutics and/or decreasing toxicity of one or more chemotherapeutic treatments by identifying a subject having one or more cancer cells; administering to the subject one or more chemotherapeutics; administering to the subject a pharmaceutically effective amount of an inhibitor compound having one of the following formulas:

7
-continued

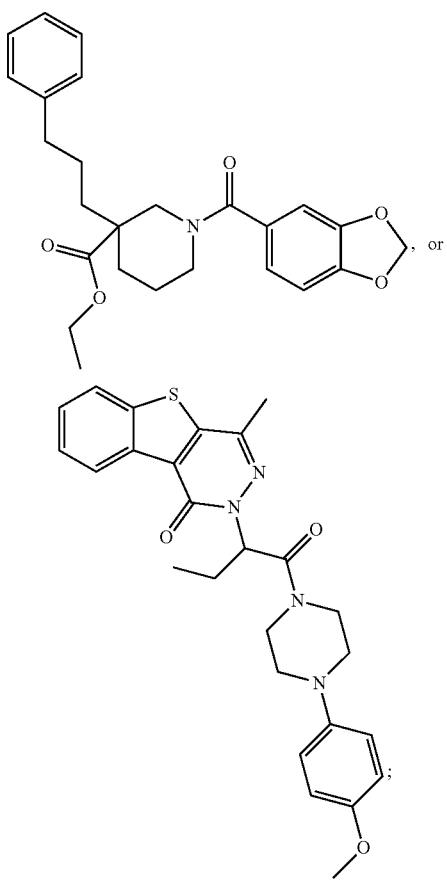

, or and contacting one or more cancer cells with the inhibitor compound to reduce the export of the inhibitor compound from the one or more cancer cells and to block the transport of the one or more chemotherapeutics from the one or more cancer cells to increasing the efficacy of the one or more chemotherapeutics and/or decreasing toxicity of the one or more chemotherapeutic treatments.

The present disclosure provides a method of increasing the penetration of an agent through the blood brain barrier or the blood testis barrier by identifying a subject in need of increasing the penetration of an agent through the blood brain barrier or the blood testis barrier; administering to the subject a pharmaceutically effective amount of an inhibitor compound having one of the following formulas:

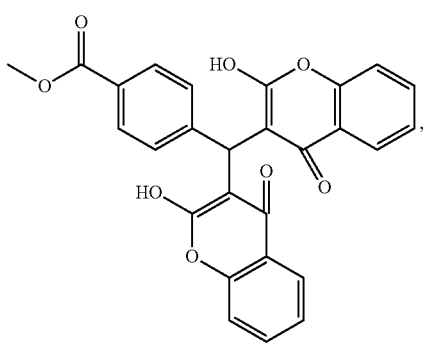

8
-continued

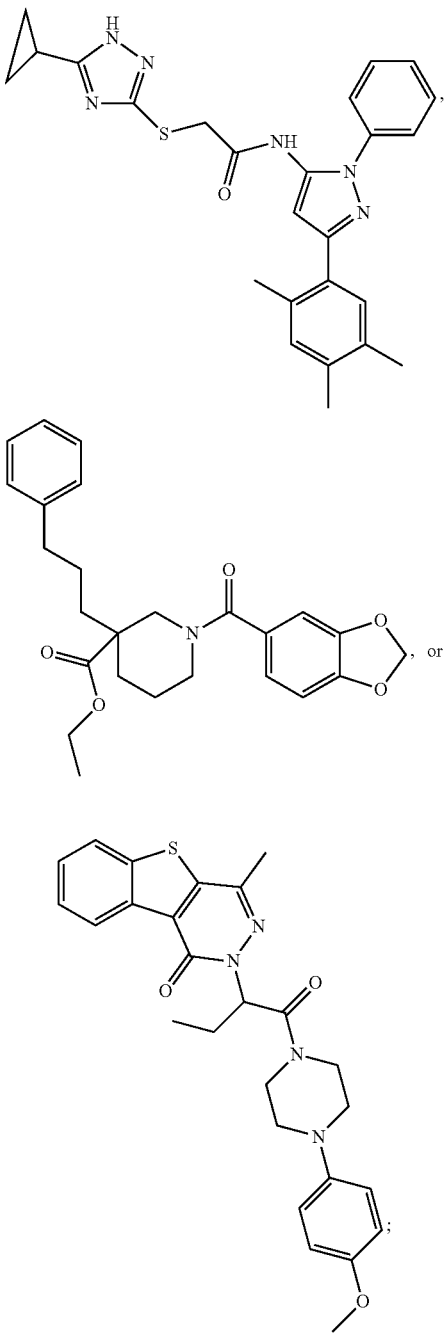

and wherein the inhibitor compound reduces the export of the inhibitor compound from the one or more cells and increases the penetration of the agent through the blood brain barrier or the blood testis barrier.

The present disclosure provides a method of decreasing the P-glycoprotein activity of a cancer patient who has built up resistance to a therapeutically active agent used in the treatment of cancer to reduce the resistance to further treatment with the substance by administering to a cancer patient before further treatment, during treatment or after treatment with the therapeutically active agent, an amount of an inhibitor compound having one of the following structural formulas:

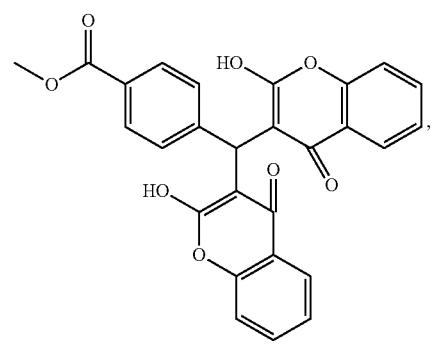

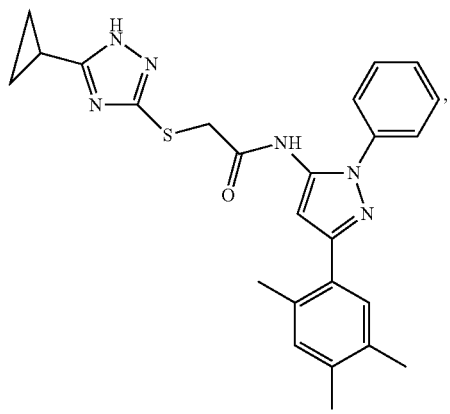

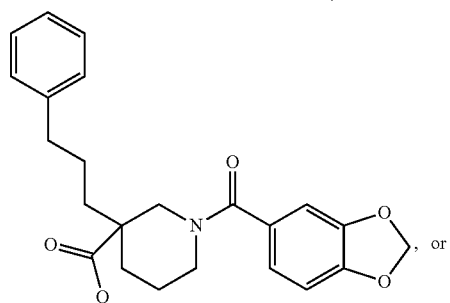, or

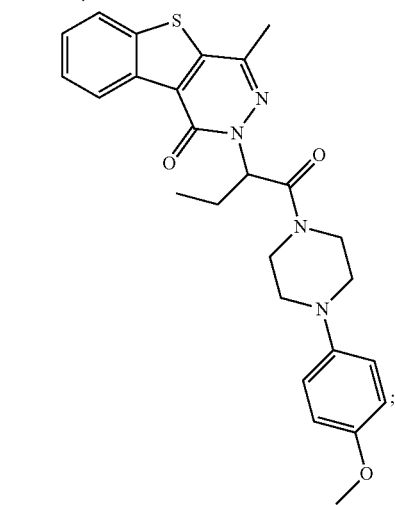;

and to reduce the export of the inhibitor compound, and to block the transport of the therapeutically active agent from one or more cancer cells of the cancer patient.

The present disclosure provides a method of reducing the likelihood of developing a resistance to a therapeutically active agent by administering to a patient before further treatment, during treatment or after treatment with the therapeutically active agent, an amount of an inhibitor compound having one of the following structural formulas:

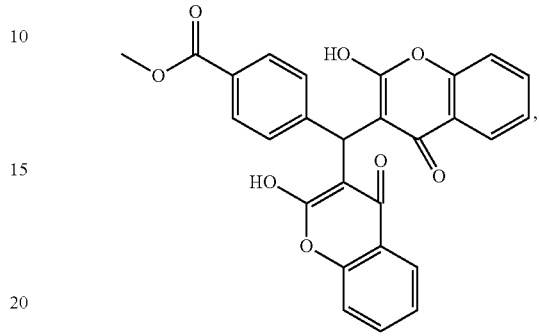

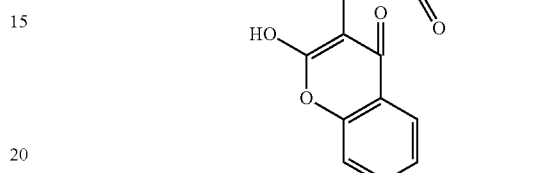,

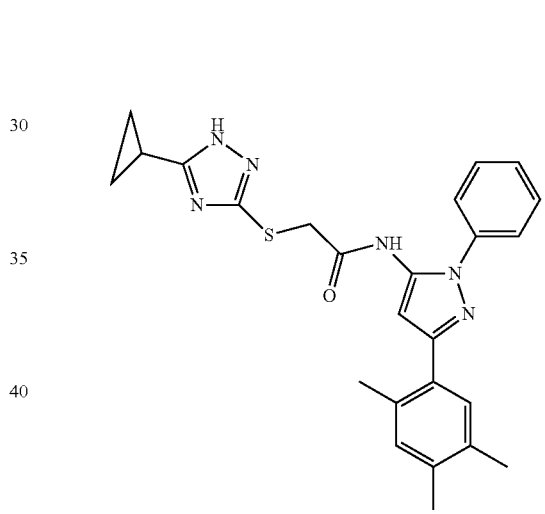, or

11
-continued

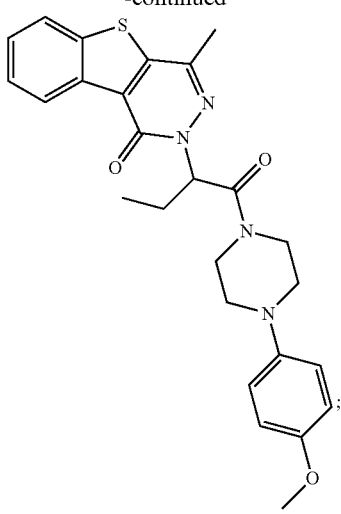

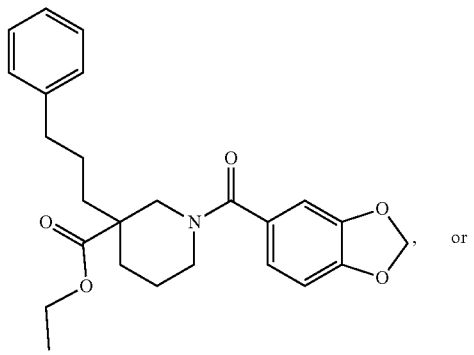

and to reduce the export of the inhibitor compound and to block the transport of the therapeutically active agent from one or more cells of the 1 patient.

The present disclosure provides a method for modulating the activity of a cell membrane transporter in a biologic tissue by contacting a tissue having a cell membrane transporter with a pharmaceutically effective amount of an inhibitor compound having one of the following structural formulas:

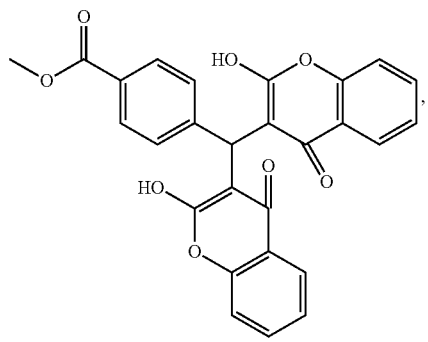

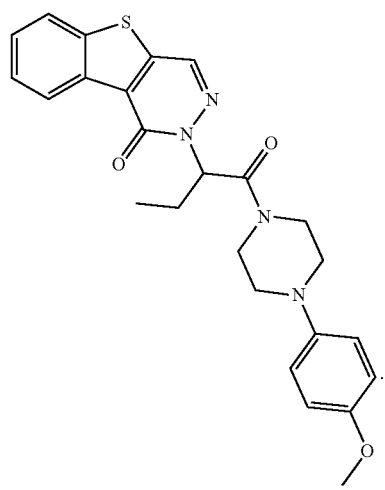

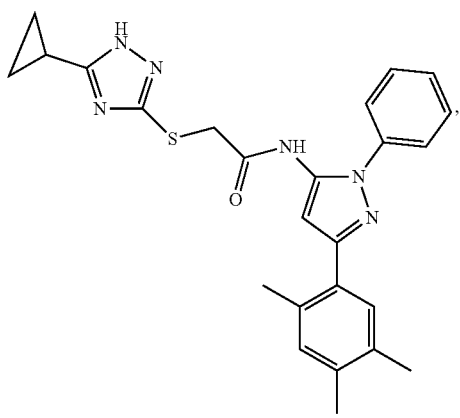

The present disclosure provides a method for treating a disease or condition in a mammal or avian resulting from an activity of a cell membrane transporter by administering to said mammal or avian a therapeutically effective amount of a pharmaceutical composition having the structural formulas:

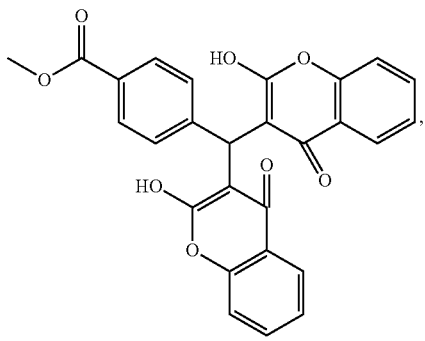

-continued

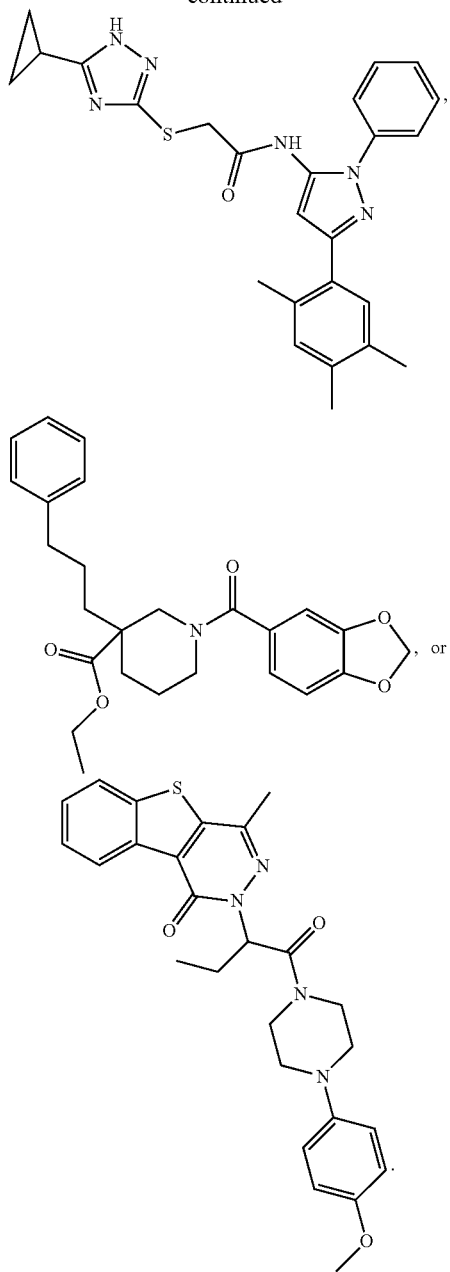

or pharmaceutically acceptable salts thereof and a pharmaceutically acceptable excipient.

BRIEF DESCRIPTION OF THE DRAWINGS

For a more complete understanding of the features and advantages of the present invention, reference is now made to the detailed description of the invention along with the accompanying FIGS. and in which.

DETAILED DESCRIPTION OF THE INVENTION

Figure 1A:
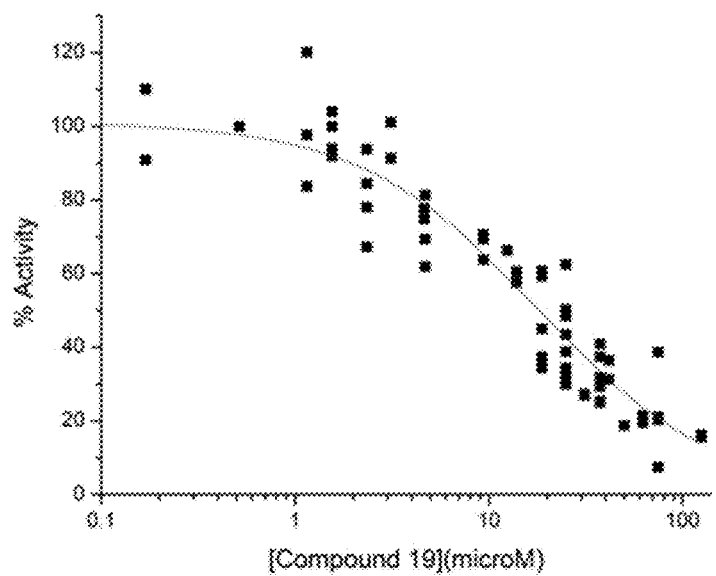
FIGS. 1A-1D are plots showing the inhibition of ATP hydrolysis by in silico identified compounds. The FIG. shows the concentration dependence of inhibition of the four identified inhibitor compounds (abbreviated 19, 29, 34 and 45). Each plot represents the composite results of 3 to 5 individual studies performed on three different P-glycoprotein preparations.
Figure 1B:
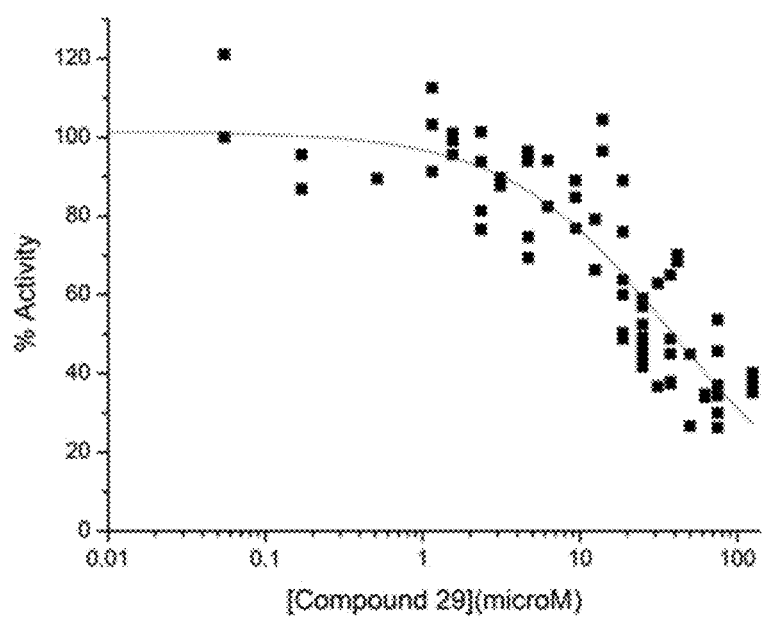
Figure 1C:
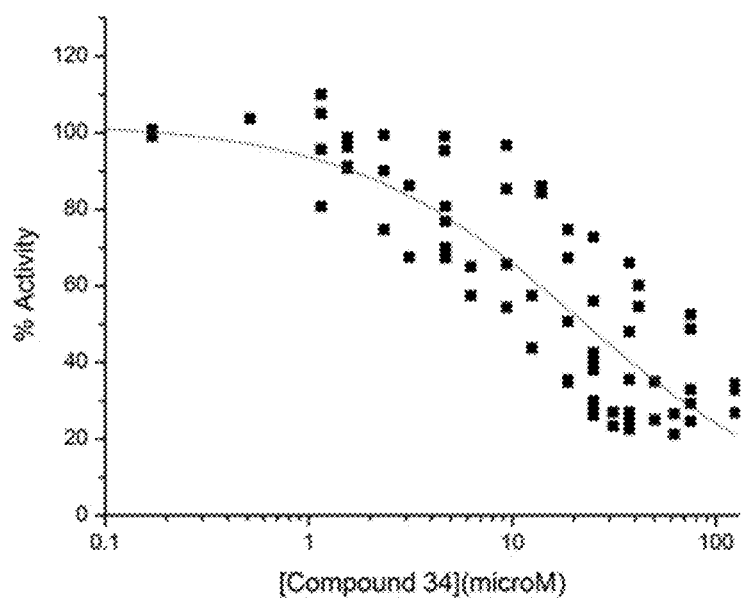
Figure 1D:
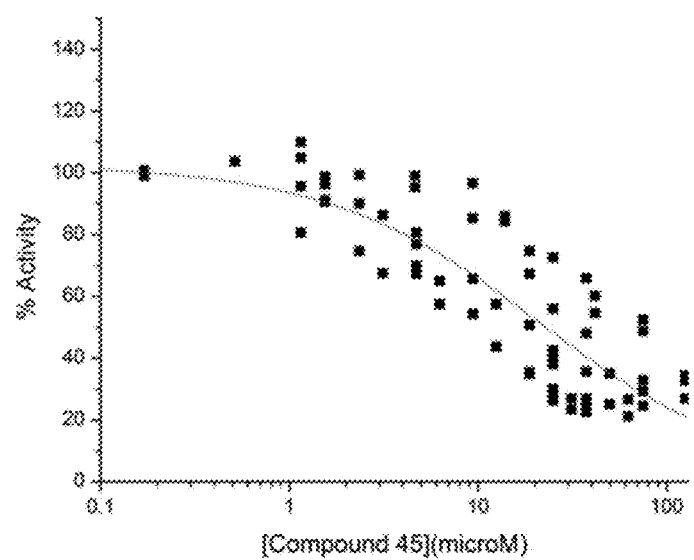
Figure 2A:
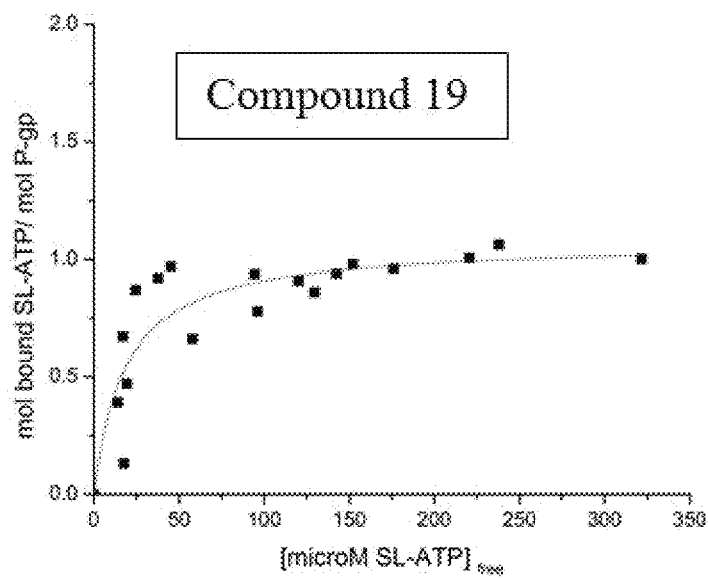
FIGS. 2A-2D are plots showing the effects of P-glycoprotein ATP hydrolysis inhibitors on nucleotide binding. Between 30 and 50 microM P-glycoprotein were incubated with 50 microM inhibitor compound. Increasing amounts of SL-ATP were added. The ESR signal of the free SL-ATP in the presence of P-glycoprotein and inhibitor was compared to that in the absence of P-glycoprotein. The graphs represent at least 3 individual studies each using 3 to 5 different P-glycoprotein preparations.
Figure 2B:
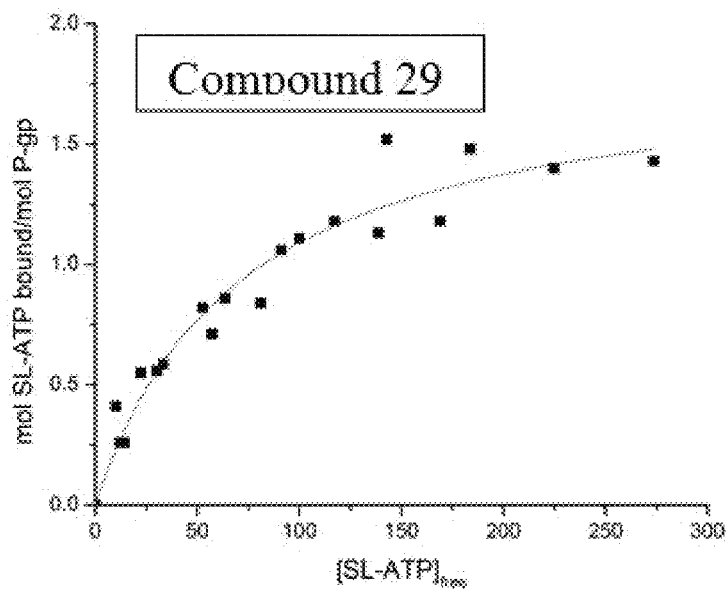
Figure 2C:
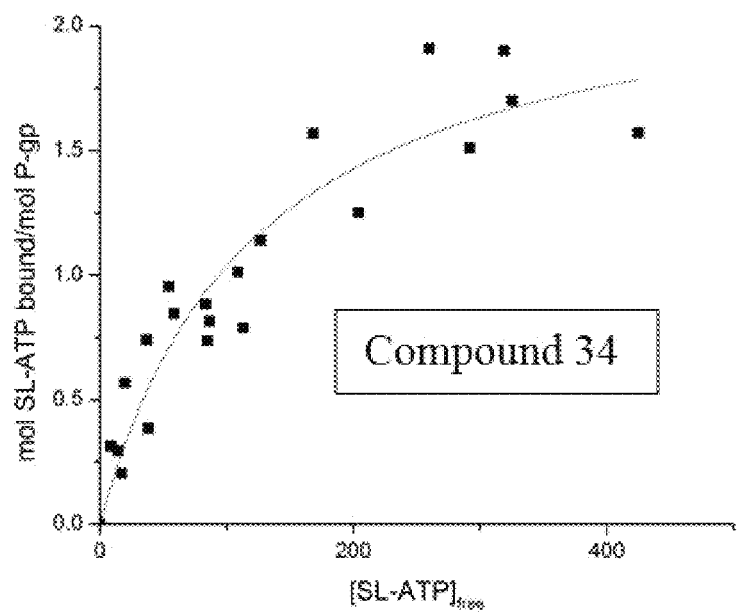
Figure 2D:
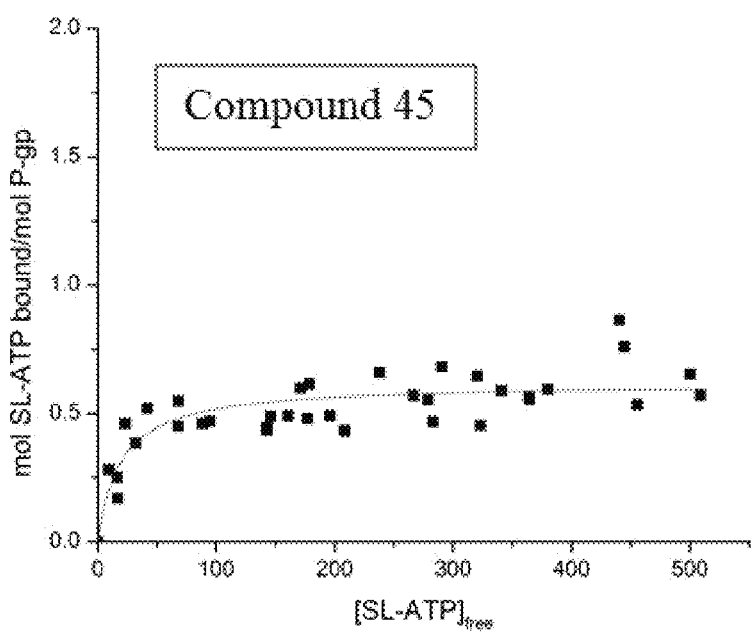

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "alkyl" denotes optionally substituted straight chain and branched hydrocarbons having about 1 to about 50 carbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

As used herein, the term "alkenyl" includes optionally substituted straight chain and branched hydrocarbon radicals having about 1 to about 50 carbons as above with at least one carbon-carbon double bond (sp2). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

As used herein, "Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. As used herein, the term "alkoxy" includes an optionally substituted straight chain or branched alkyl group having about 1 to about 50 carbons with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO2. Heteroalkyl includes alkoxy, aminoalkyl, thioalkyl, and so on. The term "alkoxy" denotes —OR—, wherein R is alkyl.

As used herein, "Substituted alkoxy" refers to the group "substituted alkyl-O—".

As used herein, the term "alkylcarbonyl" denote an alkyl group of the formula —C(O)Rc wherein Rc is alkoxy, substituted with a C(O) group, for example, CH3 C(O)—, CH$_3$CH$_2$C(O)—, etc.

As used herein, "Alkanoate" refers to "alkyl-C(=O)—O—" which includes, by way of example, ethanoate and pentanoate. "Alkyl-Alkanoate" refers to "-alkyl—O—C(=O)alkyl" such as in —CH(CH$_2$CH$_3$)—O—C(=O)—CH$_3$.

As used herein, "Alkylcarbonylalkoxy" refers to alkyl-C(=O)—O-alkyl. In one variation, the alkylcarbonylalkoxy refers to a moiety C$_1$-C$_4$ alkyl-C=O)—O—C$_1$-C$_6$ alkyl. An exemplary alkylcarbonylalkoxy is —CH$_2$CH$_2$C(=O)OCH$_3$.

As used herein, the term "alkylcarboxyl" denote an alkyl group as defined above substituted with a C(O)O group, for example, CH$_3$C(O)O—, CH$_3$CH$_2$C(O)O—, etc.

As used herein, "Carbonylalkyl" refers to —C(=O)-alkyl, which includes, by way of example, C(=O)—CH$_2$CH$_3$.

As used herein, the term "carboxy" refers to the group —C(O)OH.

As used herein, the term "carboxyl" denotes —C(O)O—, and the term "carbonyl" denotes —C(O)—.

As used herein, "C$_3$-C$_8$ monocyclic cycloalkyl" as used herein is a 3-, 4-, 5-, 6-, 7- or 8-membered saturated non-aromatic monocyclic cycloalkyl ring. Representative C$_3$-C$_8$ monocyclic cycloalkyl groups include, but are not limited to, cyclopropyl, cyclobutyl, cyclopentyl, cyclohexyl, cycloheptyl and cyclooctyl. In one embodiment, the C$_3$-C$_8$ monocyclic cycloalkyl group is substituted with one or more of the following groups: -halogen, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_3$-C$_8$ monocyclic cycloalkyl is unsubstituted.

As used herein, "C$_3$-C$_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a C$_3$-C$_8$ monocyclic cycloalkenyl group, the carbon atom to which the two groups are attached remains tetravalent. Representative C$_3$-C$_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, 1,3,5-cycloheptatrienyl, cyclooctenyl, 1,3-cyclooctadienyl, 1,4-cyclooctadienyl, or 1,3,5-cyclooctatrienyl. In one embodiment, the C$_3$-C$_8$ monocyclic cycloalkenyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_3$-C$_8$ monocyclic cycloalkenyl is unsubstituted.

The term "3- to 7-membered monocyclic heterocycle" refers to: a 3-, 4-, 5-, 6-, or 7-membered aromatic or non-aromatic monocyclic cycloalkyl in which 1-4 of the ring carbon atoms have been independently replaced with an NH, an O, or an S moiety. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the 3- to 7-membered monocyclic heterocycle is unsubstituted.

The phrases "therapeutically effective amount" and "effective dosage" denotes an amount sufficient to produce a therapeutically (e.g., clinically) desirable result; the exact nature of the result will vary depending on the nature of the disorder being treated. For example, where the disorder to be treated is cancer, the result can be the reduction of cancerous cells including cancerous tumors or the amelioration of symptoms related to the cancer cells. The compositions described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

As used herein, the term "treatment" denotes the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The term "optional" or "optionally" denotes that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical and/or synthetically non-feasible.

As used herein, the terms "patient," "subject" and "individual" are used interchangeably herein, and denote a mammalian subject to be treated, with human patients being preferred. In some cases, the methods of the invention find use in experimental animals, in veterinary applications, and in the development of animal models for disease.

As used herein, the term "chemotherapeutic agent" includes agents such as drugs which can advantageously be administered to the tissue, such as anti-tumor drugs such as paclitaxel, doxorubicin, and other drugs which have been known to affect tumors. It also includes agents which modulate other states which are related to tissues which can be permeabilized using the methods and compositions of the invention. The chemotherapeutic agent can be, for example, a steroid, an antibiotic, or another pharmaceutical composition. Examples of chemotherapeutic agents include agents such as paclitaxel, doxorubicin, vincristine, vinblastine, vindesine, vinorelbin, taxotere (DOCETAXEL), topotecan, camptothecin, irinotecan hydrochloride (CAMPTOSAR), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (ARA-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluoromethyl) propionanilide, Herceptin, anti-CD20 (Rituxan), interferon alpha, interferon beta, interferon gamma, interleukin 2, interleukin 4, interleukin 12, tumor necrosis factors, and radiation.

As used herein, the term "delivering" denotes making the composition available to the interior of the tissue (e.g., cancer cells, tumor, bacterial cell, etc.) to be treated such that the composition is capable of having a therapeutic effect on the interior of the tissue and includes, for example, contacting the tissue with the agent. The term "delivering" is intended to include administering the composition to the patient as a separate dose, as well as administering the composition to the patient together with (i.e., at the same time as or in the same dose as) other agents.

As used herein, the terms "proliferative disorder", "hyperproliferative disorder," and "cell proliferation disorder" are used interchangeably to mean a disease or medical condition involving pathological growth of cells. Such disorders include cancer.

As used herein, the terms "Cytotoxic agents" refer to compounds which cause cell death primarily by interfering directly with the cell's functioning or inhibit or interfere with cell mitosis, including alkylating agents, tumor necrosis factors, intercalators, microtubulin inhibitors, and topoisomerase inhibitors. Examples of cytotoxic agents include, but are not limited thereto, cyclophosphamide ifosfamide, hexamethylmelamine, tirapazimine, sertenef, cachectin, ifosfamide, tasonermin, lonidamine, carboplatin, mitomycin, altretamine, prednimustine, dibromodulcitol, ranimustine, fotemustine, nedaplatin, oxaliplatin, temozolomide, doxorubicin heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(c-hloro)-platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin. "mTOR inhibitors" are a subset of the cytotoxic agents and refer particularly to inhibitors of the mTOR-Raptor complex. Included in the definition of mTOR inhibitors are anti-cancer agents such as rapamycin and its derivatives, sirolimus, temsirolimus, everolimus, zotarolimus and deforolimus. Examples of microtubulin inhibitors include paclitaxel (TAXOL®), vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5 6-pentafluoro-N-(-3-fluoro-4-methoxyphenyl)benzene sulfonamide, anhydrovinblastine, N,N-dimethyl-L-valyl-L-valyl-N-methyl-L-valyl-L-prolyl-L-proline-t-butyla-mide, TDX258, and BMS 188797. Some examples of topoisomerase inhibitors are topotecan, hycaptamine, irinotecan, rubitecan, 6-ethoxypropionyl-3',4'-O-exo-benzylidene-chartreusin, 9-methoxy-N, N-dimethyl-5-nitropyrazolo[3,4,5-kl]acridine-2-(6H)pro-panamine, 1-amino-9-ethyl-5-fluoro-2,3-dihydro-9-hydroxy-4-methyl-1H,12H benzo[de]pyrano[3',4':b,7] indolizino[1,2b]quinoline-10,13(9H,15H) dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazo-le-1-carboxamide, asulacrine, (5a,5aB,8aa,9b)-9-[2-[N-[2-(dimethylamino)-ethyl]-N-methylamino]ethyl]-5-[4-Hydroxy-3,5-dimethoxyphenyl]-5,5a,6,8,8a,-9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridiniu-m, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-py-razolo[4,5,1-de]acridin-6-one, N-[1-[2(diethylamino)ethylamino]-7-methoxy-9-oxo-9H-thioxanthen-4-ylmethy-l]formamide, N-(2-(dimethylamino)ethyl)acrid-ine-4-carboxamide, 6-[[2-(dimethylamino)ethyl]amino]-3-hydroxy-7H-indeno[2-,1-c]quinolin-7-o-ne, and dimesna.

As used herein, the term "tumor" denotes abnormally growing tissue of any tissue type and includes both benign and malignant tumors, such as cancerous tumors. Examples of cancerous tumors include sarcomas, carcinomas, adenocarcinomas, lymphomas, and leukemias. The cancerous tumor may comprise metastatic lesion. It also includes any other tumors which can be advantageously treated using the methods and compositions of the invention. The cancerous tumor may be, for example, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma; non-small cell lung carcinoma, bladder carcinoma, epithelial carcinoma, glioma, astrocytoma, medulloblastoma, craniopharyngioma, ependymoma, pinealoma; hemangioblastoma, acoustic neuroma, oligodendroglioma, meningioma, melanoma, neuroblastoma, retinoblastoma, leukemia, lymphoma, or Kaposi's sarcoma.

Cellular membranes form a selective permeability barrier to ions and molecules thereby maintaining intracellular concentrations that are compatible with and optimized for physiological processes. This permeability barrier is comprised of a lipid bilayer, which restricts the passage of polar, charged and hydrophilic molecules and ions, and of cell membrane transporters. Cell membrane transporters include proteinaceous structures that open in a controlled manner to allow selected ions or small molecules to flow passively into or out of the cell (e.g., ion channels), other proteins that allow the facilitated diffusion of larger polar molecules down their concentration gradients (e.g. facilitated transport of glucose), and proteins that actively pump ions and molecules into or out of the cell against a concentration gradient (e.g., $H^+/K^+$ ATPases, MDR efflux pumps, neurotransmitter transporters).

Ion channels serve a variety of important cellular functions, including excitability, neuronal signaling, excitation-secretion coupling, volume regulation and so on and are formed by the association of integral membrane proteins into structures having a central hydrophilic pore. Channel pores allow ions to equilibrate across membranes in response to their electrochemical gradients and at rates that are diffusion-limited and are characterized by their selectivity and gating properties. Selectivity refers to the rate at which different ion species pass through an open channel under standard conditions. Gating is the process that regulates the opening and closing of an ion channel. Thus, voltage-regulated ion channels respond to changes in membrane potential; ligand-regulated channels respond to the binding of particular neurotransmitters or intracellular messengers; and mechanosensitive channels respond to mechanical deformation. Ion channels exist in resting (closed), open or inactivated (i.e., desensitized) states. Voltage-gated ion channels in the open state typically transition to an inactivated state, and must reacquire the ability to respond to an external stimulus during a recovery period. This may also be true of ligand-gated channels, particularly after prolonged exposure to an agonist. Certain channels are gated by more than one type of stimulus (e.g., an inward rectifying voltage-regulated potassium channel in cardiac muscle is activated by acetylcholine).

The ABC transporters comprise a superfamily that shares a highly conserved ATP-binding cassette. These transporters typically use ATP hydrolysis as a source of energy to pump diverse classes of molecules (e.g., sugars, peptides, inorganic ions, amino acids, oligopeptides, polysaccharides, proteins) across membranes against a concentration gradient. Some transporters are highly selective for a particular substrate and pump unidirectionally, and some members of the ABC transporter family have ion channel activity. For example, the cystic fibrosis transmembrane regulator (CFTR), a cAMP- and protein kinase A-regulated $Cl^-$ channel, uses ATP hydrolysis as a gating mechanism. P-glycoprotein (MDR) appears to be bifunctional, possessing drug transport as well as chloride channel activities; the latter is cell-volume regulated and requires the binding, but not the hydrolysis, of ATP. In both prokaryotes and eukaryotes, ABC transporters function in nutrient uptake, protein export and drug resistance (e.g., erythromycin resistance in Staphylococcus, daunomycin resistance in Streptomyces, chloroquine resistance in Plasmodium, and multidrug resistance in cancers). Ion pumps are also involved in the active transport of ions across membranes. Ion pumps can be members of the ion-transporting P-type ATPase family which couple ion transport to a cycle of phosphorylation and dephosphorylation of an ATPase enzyme. In mammalian cells, this class includes the $Ca^{2+}$ATPases, the $Na^+/K^+$ ATPases, and the $H^+/K^+$ ATPases; however, V-ATPase is not a member of the ion-transporting P-type ATPase family. The $H^+/K^+$ ATPases are involved in acid secretion in the stomach, and are clinically important targets in peptic ulcer disease, gastroesophageal reflux disease (GERD) and gastric hyperacidity. The $Ca^{+2}$ and $Na^+/K^+$ ATPases are therapeutic targets in the treatment of heart failure.

Cancer and cancer chemotherapies. For blood cell cancers like lymphomas and leukemias, chemotherapies remain the primary methods of treatment. At the current time there are about 100 different chemotherapeutic drugs that have been approved for use against cancers in humans in the United States. Different drugs or different combinations of drugs are being used against different cancers. Chemotherapies have proven extremely valuable in many cases. For example, childhood cases of acute lymphocytic leukemia, a cancer of the blood that presents with uncontrolled multiplication of a type of white blood cells, once a veritable death sentence, are now often curable.

Unfortunately, such positive outcomes are not always achieved. In fact, cancer remains the third leading cause of death, despite many advances in recent years. One problem is that many times, after what appears to be a successful chemotherapy, the cancer recurs and is again detected in the patient. Such chemotherapy failures may have several causes. One major cause is that a family of proteins that remove the chemotherapeutic drugs from subpopulations of the cancerous cells is overly produced (i.e., "over-expressed") in these cells. These proteins are members of a class of membrane bound transporter proteins, called ABC transporters that act like cellular vacuum cleaners. They are aptly called multidrug resistance proteins or MDR pumps. The over-expression of one specific member of these MDR pumps, a protein called P-glycoprotein, seems to be especially important for cancers that become resistant to chemotherapeutics. Other proteins that are closely related to the P-glycoprotein, are also thought to be involved in other chemotherapy failures.

P-Glycoprotein normally functions as a biochemical transporter that is able to bind a great variety of toxic chemicals inside of the living cell and, using a chemical power source called ATP, pushes the toxin through the cell membrane. This action effectively removes the toxin from the cells. The pump is therefore an essential component in important tissue boundaries like the blood-brain and blood-testis barriers. It is also helpful for the detoxification of important tissues and organs like breast, ovaries and kidneys. While this normally very important function of P-glycoprotein keeps cellular toxins at a low concentration in our cells and tissues, it is thought to be one of the root causes for cancer chemotherapy failures. For example, if a subset of cancer cells produces enough of this protein to cause the effective concentration of cancer chemotherapeutic(s) inside the cancerous cells to fall below the threshold(s) for clinical efficacy, then members of this subset of cancerous cells will survive the therapy. Once multiplying, this subset of cancerous cells will form a recurrent or relapsed cancer that consists of or contains cells that are resistant to chemotherapeutic drugs.

Because toxin pumps like the P-glycoprotein have evolved to export a wide variety of cellular toxins from the body's cells, they do not exhibit specificity towards a particular chemical compound or toxin and are capable of removing a wide variety of different toxins, drugs and chemotherapeutic compounds from the inside of the cell. Because of this latter property, when P-glycoprotein or one of its close relatives are the cause of chemotherapy failure, the recurrent cancer becomes resistant to many of the chemotherapeutics available, not just the one(s) used during original therapy. These recurrent cancers are now "multidrug resistant."

Typically, a small percentage of the original cancer cells develop mutations that instruct these few cells to produce more than a normal complement of P-glycoprotein. During chemotherapy, all or nearly all of the cancer cells that express low or moderate amounts of P-glycoprotein are killed, but the cells that produce high amounts of P-glycoprotein survive. These survivors then multiply over time and the cancer grows back. What is different, however, is that all of the cells of the recurring cancer are now over-expressing P-glycoprotein transport activity and are therefore resistant to nearly all chemotherapies.

P-glycoprotein was linked as a cause of chemotherapy resistances in cancer nearly 30 years ago. Scientists have been searching in vain for small molecule inhibitors of this transporter that would serve to decrease the active export of chemotherapeutics from resistant cancer cells. The inhibition of P-glycoprotein of the present invention serves to re-sensitize the resistant cells to new rounds of chemotherapy, rendering the ineffective chemotherapies once more effective.

Most often in the past, inhibitors of P-glycoprotein have been found that interacted with the drug transporting parts of the protein. By competing with the chemotherapeutic for binding to and being transported by the pump, these inhibitors slow down the export of the chemotherapeutic drug. The problem with these types of P-glycoprotein inhibitors is that high concentrations of inhibitors are then required to get enough inhibitor into the cell to effectively slow or stop P-glycoprotein if the inhibitors are transport substrates themselves. With the required high concentrations of inhibitors come additional or worsened side-effects caused by the P-glycoprotein inhibitors themselves. These side effects have led to the failure of the previously identified inhibitors in clinical trials and have led to problems with their translation into therapeutic regimens. Thus, the long felt need is unresolved in spite of numerous attempts.

Stem cells are an important subset of the cells in all multicellular organisms and have been found in a variety of mammalian tissues. These cells are of paramount importance for regeneration and repair of damaged tissues since they can either self-renew or differentiate to replace damaged cells. Importantly, stem cells display a property of durable self-renewal or the ability to divide and reproduce many times without differentiation into a mature cell type.

Cancer stem cells (CSCs) have been defined as stem cell like cells within a population of cancerous cells that can renew and propagate the cancer; much like normal stem cells can propagate and renew cells of normal tissues. A key difference of course is that the cancer stem cells have the acquired mutations and chromosomal alterations that lead to the uncontrolled proliferation of the cancer. Some researchers have noted that the durability of the reservoir of cells that compose a normal or cancer stem cell population needs a constant and high level of expression of multidrug transporter proteins to maintain a protected state of the cell, i.e. a state that makes it unlikely that the stem cells will be killed by incidental chemical exposure. In recent years, this constant over-expression of P-glycoprotein in cancer stem cells has indeed been found to be the case.

One of the great problems that cancer stem cells present is that even if the vast majority of a cancerous population of cells is sensitive to chemotherapeutics and is killed by the chemotherapy, the fact that multidrug transporters like P-glycoprotein are highly expressed in the cancer stem cell population allows these cells to survive the chemotherapy. They will ultimately renew and repopulate the cancer. This scenario presents the physician and patient with a seemingly initial success of the therapy, followed ultimately by a recurrence of the cancer, a cancer that now consists mostly of cells that are resistant to chemotherapy.

Effective inhibition of P-glycoprotein in the context of initial cancer chemotherapy is therefore likely to also make the cancer stem cell population more sensitive to the cell toxicity of the chemotherapeutic. Co-administering of P-glycoprotein inhibitors with the chemotherapeutic may therefore be a method of treating not only drug resistant cancers but also leads to the diminution of the cancer stem cell population within the patient. This result strongly increases the therapeutic index of the chemotherapy by preventing recurrence through the cancer stem cell population route.

The blood brain barrier (BBB) which serves to separate the blood from the extracellular fluid of the brain and spinal cord, i.e. central nervous system (CNS), is created by a special capillary cell construction found only in these organs. The cells of the circulatory system in other tissues are normally not tightly associated, which allows a much freer diffusion of substances out of the blood capillary and into the tissues of the neighboring organ. In the brain and spinal cord, however, the endothelial cells that make up the capillary vessels are connected by tight junctions that prohibit such free diffusion between cells. For compounds that are larger than small hydrophobic molecules like oxygen and carbon dioxide, to enter the brain, they must diffuse into, across, and out of the endothelial barrier cells that make up the capillary. These cells, however, express a large amount of P-glycoprotein in the luminal membranes. This severely inhibits movement of drugs into the brain, since P-glycoprotein transports them back into the lumen of the capillary as soon as they appear in the cytoplasm of the capillary cells. P-glycoprotein therefore represents an essential part of the BBB system, and is responsible for the poor brain penetration of many important pharmacotherapeutics. These properties of the BBB, most especially the high expression of P-glycoprotein in the cells making it up, severely decrease the utility of therapeutics when the target organ is part of the CNS.

Numerous examples of the problems presented by P-glycoprotein in getting effective therapies into the brain have been reported showing an unmet need for such therapies. As an example, over-expression of P-glycoprotein in the BBB of drug-resistant epilepsy patients has been observed and about one-third of all epilepsy patients exhibit drug-resistance.

In a cancer related example, a receptor tyrosine kinase inhibitor called imatinib has been shown in cell culture studies to be very effective in inhibiting the growth of glioma cells, but the very poor penetration of the BBB by imatinib results in very limited efficacy in patients. These researchers showed that the poor brain penetration of imatinib was due to P-glycoprotein. It should be noted that gliomas make up about 30% of all brain tumors and nearly four fifths of all malignant brain tumors.

Effective inhibition of P-glycoprotein in the context of the pharmacological penetration of the blood brain barrier by therapeutics that are excluded from the brain by the P-glycoprotein component of the BBB would increase the efficacy of these agents. Co-administration of such a P-glycoprotein inhibitor with the normally brain-excluded drug would allow these drugs to enter the brain.

The methods of the present invention provide for the identification of targeted inhibition of P-glycoprotein that interrupt or alter either ATP binding or ATP hydrolysis at the nucleotide binding sites of the transporter. ATP, adenosine triphosphate, is a compound used in all living cells. The compound is able to store large amounts of energy and will release this energy upon hydrolysis of its terminal phosphate group(s) in order to perform work. P-glycoprotein has two such ATP binding sites that supply the energy required to perform the work of transporting a drug transport substrate from one side of the membrane to the other.

The methods of the present invention allow us to identify potential inhibitors that only bind to the nucleotide binding domains of P-glycoprotein and not to the drug binding sites on the protein. This eliminates the overarching problem seen with inhibitors that bind to the drug binding domain. The inhibitor molecules identified with these methods only minimally bind to the drug binding and drug transport domains of P-glycoprotein, and are therefore, only minimally transported by P-glycoprotein. This means that once the inhibitor molecules are inside the cell, they are not significantly removed from the cell by P-glycoprotein, while at the same time also blocking the chemotherapeutic drug to be exported from the cells resulting in effective therapy.

Molecular models of human P-glycoprotein and targeted in silico screening for inhibitors. Wise described the methodology and results of modeling the structural changes in human P-glycoprotein as the transporter transitions from one conformational state to another during a catalytic cycle. The computational analyses of structures that the transporter protein adopts during a drug transport cycle allowed the analysis of the interactions of millions of drug like molecules with the protein in distinct catalytically relevant conformations. Such extensive screens for specific interactions of small molecule compounds with different structural intermediates of P-glycoprotein have not been previously reported.

A subset of the database of commercially available compounds which includes molecules with drug-like characteristics was obtained from the ZINC website. These compounds were used in in silico docking studies aimed at identifying drug-like compounds that would interact strongly with the nucleotide binding domain structures of various human P-glycoprotein structural conformations. Docking studies were performed with the Autodock 4.2 program using the high performance computational facilities of the Center for Scientific Computing at Southern Methodist University.

To date about 16 million protein-small molecule drug interactions at the nucleotide binding domains of human P-glycoprotein were analyzed. Compounds that showed strong binding interactions to the P-glycoprotein nucleotide binding domain structures were further analyzed for possible interactions at the drug binding domains of P-glycoprotein again using the Autodock 4.2 programs. Ultimately, the identification of compounds that interact strongly at nucleotide binding domains but weakly at the drug binding domains of P-glycoprotein were sought. This approach identifies molecules that inhibit the catalytic transport mechanism of P-glycoprotein by disrupting ATP binding and or hydrolysis but that would not be effectively transported out of the cell by virtue of the lack of predicted interactions at the drug-toxin pumping structures of P-glycoprotein (the drug binding domains).

Several hundred molecules from the ZINC drug-like molecule database subset were found that satisfied these hypothetical requirements for P-glycoprotein inhibitors with low probabilities of being transport substrates. Of these initial molecules, 35 molecules were purchased from commercial sources and used in in vitro biochemical assays to determine the effectiveness of inhibition of catalysis by P-glycoprotein, and were used in cell-based assays to estimate toxicity of the compounds on human cells in culture. In addition, assays of sensitization and re-sensitization of human cancer cell lines that either express normally low amounts of P-glycoprotein or that over-express P-glycoprotein were performed. These latter assays actually test the compounds for their ability to overcome multidrug resistances by inhibition of the intrinsic P-glycoprotein transporter in these cancer cells.

The efficacy of molecules identified using in silico methods to function as potential inhibitors of P-glycoprotein was initially tested with regard to their capability to inhibit ATP hydrolysis by purified P-glycoprotein. For this purpose, a well-established activity assay for ATP hydrolyzing enzymes that uses the oxidation of NADH to $NAD^+$ through coupling the reactions of pyruvate kinase and lactate dehydrogenase to the hydrolysis of ATP was adapted to medium throughput conditions on 96 well plates. The decrease of NADH absorption at 340 nm light was observed in a BioTek Eon plate reader. In this set-up, the effects of potential small molecule inhibitors on the ATP hydrolysis activity of P-glycoprotein were tested in duplicate or triplicate and were repeated at least two times using different enzyme preparations.

The P-glycoprotein used in these assays was a close relative of the human P-glycoprotein that is found in mice. A mutant version of the mouse P-glycoprotein where all intrinsic cysteine amino acids had been replaced by alanine residues was recombinantly expressed in the yeast *Pichia pastoris* and used for these initial tests. Purification of the protein was achieved with small modifications resulting in highly enriched P-glycoprotein in micelles containing dodecyl maltoside and lysophosphatidyl choline as detergents. Prior to testing the ATP-hydrolysis activity, P-glycoprotein was incubated with phosphatidyl choline for stabilization of the enzyme during the assay.

ATP hydrolysis by P-glycoprotein is stimulated by transport substrates like the calcium channel blocker verapamil which was initially indicated as an inhibitor of P-glycoprotein. Verapamil inhibits pumping of chemotherapeutics from cancer cells by competing for the same binding sites as the chemotherapeutics and therefore is a transport substrate itself. Typically, 150 µM verapamil was added to the assay mixture containing purified P-glycoprotein in 96 well plates. Different concentrations of the to-be-tested small molecules were added and pre-incubated at 37° C. The ATP hydrolysis reaction was then started by adding equal volume of double concentrated ATPase cocktail. The final ATP concentration in the reaction was 2 mM. The reaction was allowed to proceed for 20 minutes, the rate of ATP hydrolysis was calculated using the molar extinction coefficient of NADH, and the one-to-one relationship of ATP hydrolyzed and NADH oxidized.

We have identified a group of compounds from in silico studies that were predicted to bind with high affinity at the nucleotide binding domains but only weakly at the drug binding domains of P-glycoprotein. Thirty-five molecules were selected as possible inhibitors of the power generating functions of P-glycoprotein and were then biochemically assayed for inhibition of ATP hydrolysis activity catalyzed by P-glycoprotein. Compounds were initially screened with 25 microM putative inhibitor as described above. Four of the 35 compounds were observed to inhibit verapamil-stimulated ATPase activities by P-glycoprotein. These compounds did not significantly stimulate basal ATP hydrolysis rates of P-glycoprotein, indicating that they did not interact with P-glycoprotein drug binding domains (data not shown).

Compounds "SMU-19", "SMU-29", "SMU-34" and "SMU-45", that were identified from the in silico screening methods that target P-glycoprotein nucleotide binding domains and exclude compounds that interact strongly with the drug binding structures as described above, were found to significantly inhibit the verapamil-stimulated ATP hydrolysis catalyzed by P-glycoprotein.

One embodiment of the present invention includes a P-glycoprotein inhibitory or binding composition having the structure:

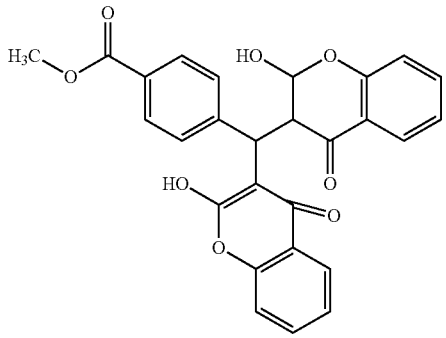 [SMILES: COC(=O)c1ccc(C(c2c(O)oc3ccccc3c2=O)C2C(=O)c3ccccc3OC2O)cc1]

The composition is also denoted as Compound SMU-19: methyl 4-[bis(2-hydroxy-4-oxochromen-3-yl)methyl]benzoate (ZINC 09973259, CID 4694077). However, the composition may include other substitutions of the core composition:

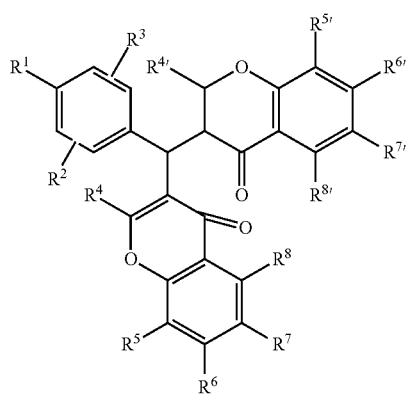

where R1, R2, R3, R4, R4', R5, R5', R6, R6', R7, R7', R8, and R8' may independently be alkyl, alkenyl, alkoxy, carboxy, carboxyl, alkylcarbonyl, alkylcarboxyl, alkanoyloxy, alkoxycarbonyl, or hydroxyl.

Another example of the P-glycoprotein inhibitor composition of the instant invention

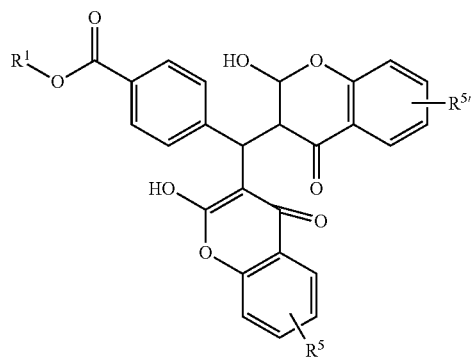

where R1 may be an alkyl (e.g., methyl, ethyl, etc.), R5, and R5' may independently be an alkyl (e.g., methyl, ethyl, etc.), substituted alkyl (e.g., $CF_3$, $CH_2F$, etc.), carboxyl, or hydroxyl.

One embodiment of the present invention includes a P-glycoprotein inhibitory or binding composition having the structure:

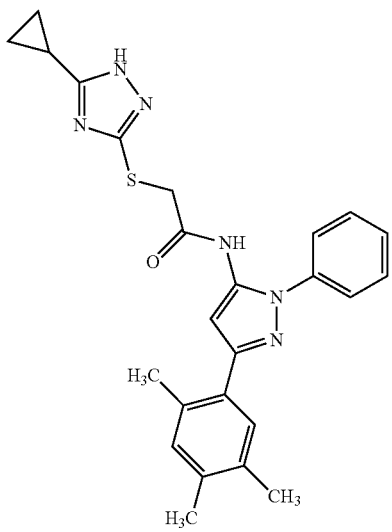 [SMILES: Cc1cc(C)c(-c2cc(NC(=O)CSc3n[nH]c(C4CC4)n3)n(-c3ccccc3)n2)cc1C]

The composition is also denoted as Compound SMU-29: 2-[(5-cyclopropyl-1H-1,2,4-triazol-3-yl)sulfanyl]-N-[2-phenyl-5-(2,4,5-trimethylphenyl)pyrazol-3-yl]acetamide (ZINC 08767731, CID 17555821); however, the composition may include other substitutions of the core composition:

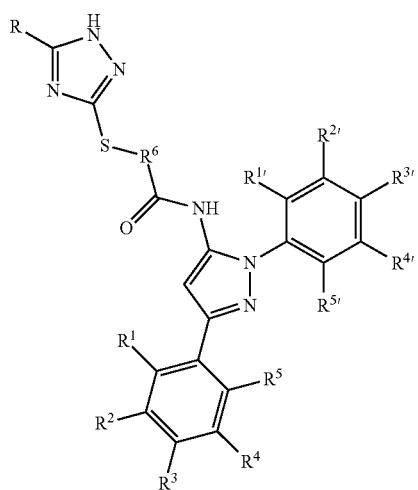

R may be a substituted or unsubstituted C3-C8 monocyclic cycloalkyl, a C3-C8 monocyclic cycloalkenyl, or a 3- to 7-membered monocyclic heterocycle; R1, R1', R2, R2', R3, R3', R4, R4', R5, and R5' may independently be alkyl, alkenyl, alkoxy, carboxy, carboxyl, alkylcarbonyl, alkylcarboxyl, alkanoyloxy, alkoxycarbonyl, or hydroxyl; R6 may be a C1-C10 alkyl.

The composition denoted as Compound SMU-29 can also have the chemical structures of SMU-29 variants:

231

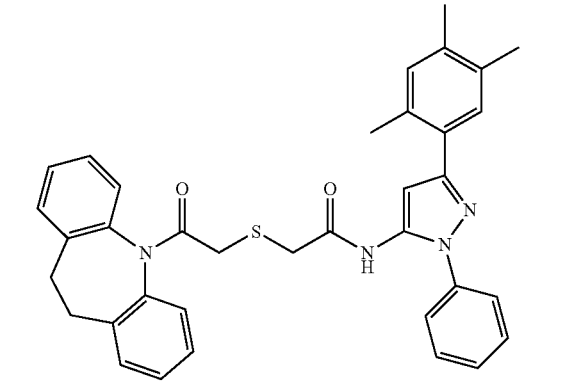

227

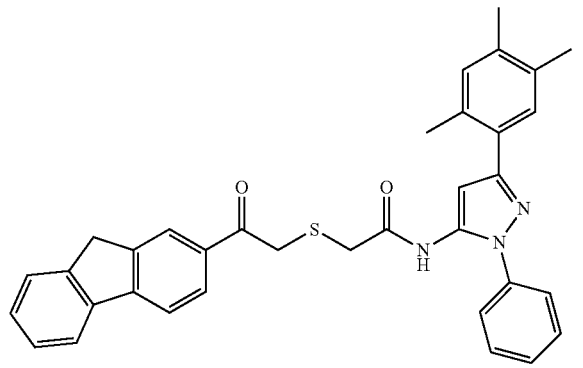

216

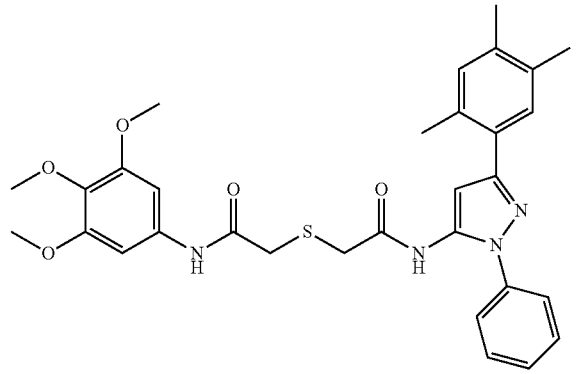

238

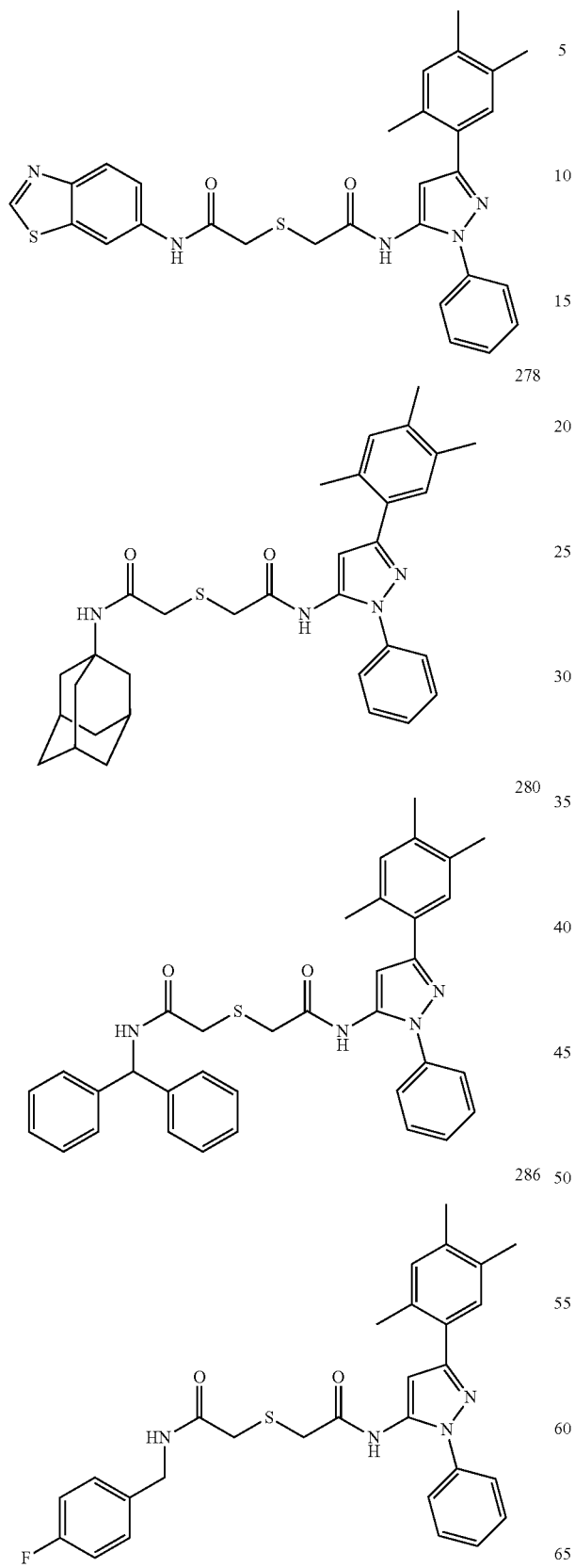

One embodiment of the present invention includes a P-glycoprotein inhibitory or binding composition having the structure:

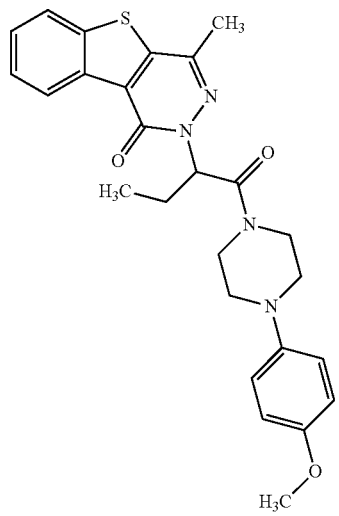 [SMILES: CCC(C(=O)N1CCN(c2ccc(OC)cc2)CC1)n1nc(C)c2sc3ccccc3c2c1=O]

The composition is also denoted as Compound SMU-34: 2-[1-[4-(4-methoxyphenyl)piperazin-1-yl]-1-oxobutan-2-yl]-4-methyl-[1]benzothiolo[2,3-d]pyridazin-1-one (ZINC 09252021, CID 22514118); however, the composition may include other substitutions of the core composition:

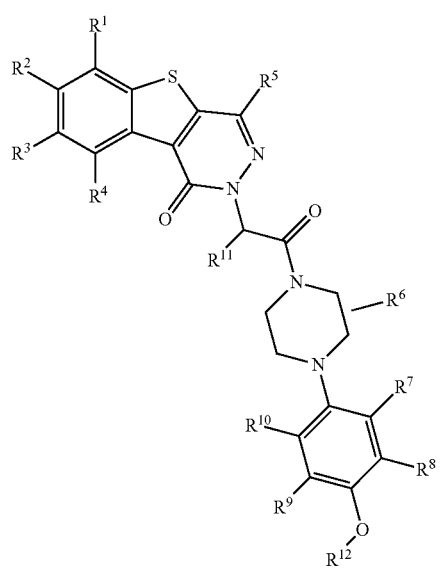

where R1, R2, R3, R4, R5, R6, R7, R8, R9, R10 and R11 may independently be alkyl, alkenyl, alkoxy, carboxy, carboxyl, alkylcarbonyl, alkylcarboxyl, alkanoyloxy, alkoxycarbonyl, or hydroxyl.

One embodiment of the present invention includes a P-glycoprotein inhibitory or binding composition having the structure:

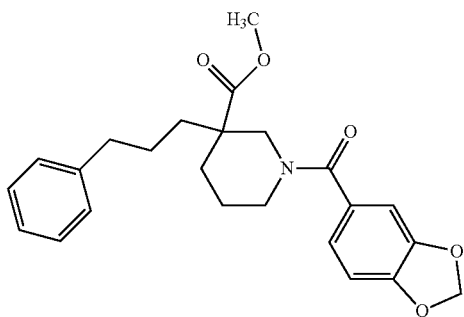 [SMILES: COC(=O)C1(CCCc2ccccc2)CCCN(C(=O)c2ccc3c(c2)OCO3)C1]

The composition is also denoted as Compound SMU-45: ethyl 1-(1,3-benzodioxole-5-carbonyl)-3-(3-phenylpropyl) piperidine-3-carboxylate (ZINC 15078148, ZINC 15078146, CID 26410703, CID 45252040); however, the composition may include other substitutions of the core composition:

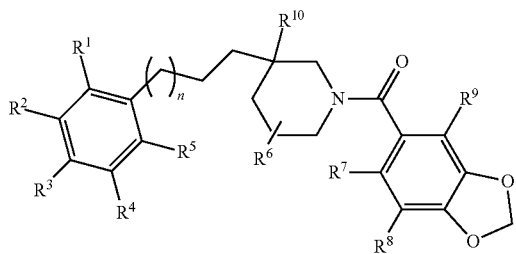

where n maybe from 0-10 and $R1$, $R2$, $R3$, $R4$, $R5$, $R6$, $R7$, $R8$, $R9$, and $R10$ may independently be alkyl, alkenyl, alkoxy, carboxy, carboxyl, alkylcarbonyl, alkylcarboxyl, alkanoyloxy, alkoxycarbonyl, or hydroxyl. For example, another embodiment may include the structural formula:

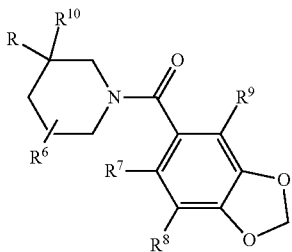

where $R6$, $R7$, $R8$, $R9$, and $R10$ may independently be alkyl, alkenyl, alkoxy, carboxy, carboxyl, alkylcarbonyl, alkylcarboxyl, alkanoyloxy, alkoxycarbonyl, or hydroxyl. R may be a substituted or unsubstituted C3-C8 monocyclic cycloalkyl, a C3-C8 monocyclic cycloalkenyl, or a 3- to 7-membered monocyclic heterocycle; and optionally connected by an alkyl, alkenyl, alkoxy, carboxy, carboxyl, alkylcarbonyl, alkylcarboxyl, alkanoyloxy, alkoxycarbonyl, or hydroxyl; $R6$ may be a C1-C10 alkyl.

These P-glycoprotein inhibitors were investigated further. FIGS. 1A-1D show the ATP hydrolysis by P-glycoprotein in the presence of varying concentrations of inhibitor compounds normalized to verapamil-stimulated P-glycoprotein activity. IC50 values for the inhibitors in these assays were observed to be about 20 microM.

FIGS. 1A-1D are plots showing the inhibition of ATP hydrolysis by in silico identified compounds. The FIG. shows the concentration dependence of inhibition of the four identified inhibitor compounds (abbreviated 19, 29, 34 and 45). Each plot represents the composite results of 3 to 5 individual studies performed on three different P-glycoprotein preparations.

Determination of the possible mode of ATP hydrolysis inhibition by the identified P-glycoprotein inhibitors. The mode of hydrolysis of ATP by P-glycoprotein was investigated by measuring the maximal binding stoichiometry and binding affinity of an analog of ATP, SL-ATP, and by Electron Spin Resonance (ESR) spectroscopy, similar to in both the presence and absence of the identified inhibitors.

ESR spectra are acquired for known concentrations of SL-ATP and compared to spectra acquired in the presence of known concentrations of P-glycoprotein, verapamil and inhibitor molecule. The high-field signal of the freely mobile, unbound SL-ATP is compared and is used to calculate the amount of ATP-analog bound to P-glycoprotein. The results of these studies are presented in FIG. 2. Binding of SL-ATP in the absence of any P-glycoprotein inhibitor saturated at about 2 mol of SL-nucleotide bounds per mol of P-glycoprotein.

FIGS. 2A-2D are plots showing the effects of P-glycoprotein ATP hydrolysis inhibitors on nucleotide binding. Between 30 and 50 microM Pgp were incubated with 50 microM inhibitor compound. Increasing amounts of SL-ATP were added. The ESR signal of the free SL-ATP in the presence of P-glycoprotein and inhibitor was compared to that in the absence of P-glycoprotein. The graphs represent at least 3 individual studies each using 3 to 5 different P-glycoprotein preparations.

Compounds SMU-19 and SMU-45 reduced the stoichiometry of binding of SL-nucleotides to P-glycoprotein. Compounds SMU-29 and SMU-34 decreased the SL-ATP binding affinities for P-glycoprotein. All four of the inhibitor compounds effected SL-ATP binding, which provides physical evidence that the in silico selection for binding of inhibitor at the nucleotide binding domains of P-glycoprotein worked as hypothesized for these compounds.

Figure 3A:
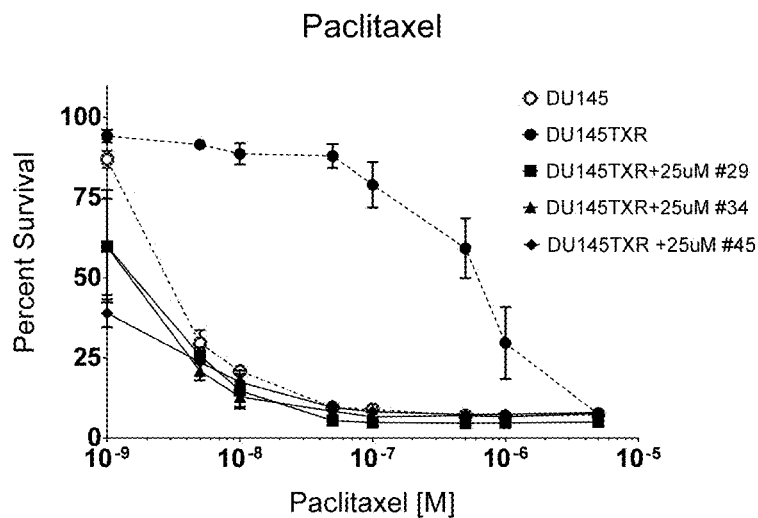
FIGS. 3A-3B are plots that show an example of the re-sensitization of a multidrug resistant prostate cancer cell line to two different chemotherapeutics using the prostate cancer derived cell line, DU145 and the multidrug-resistant variant, DU145-TxR.
Figure 3B:
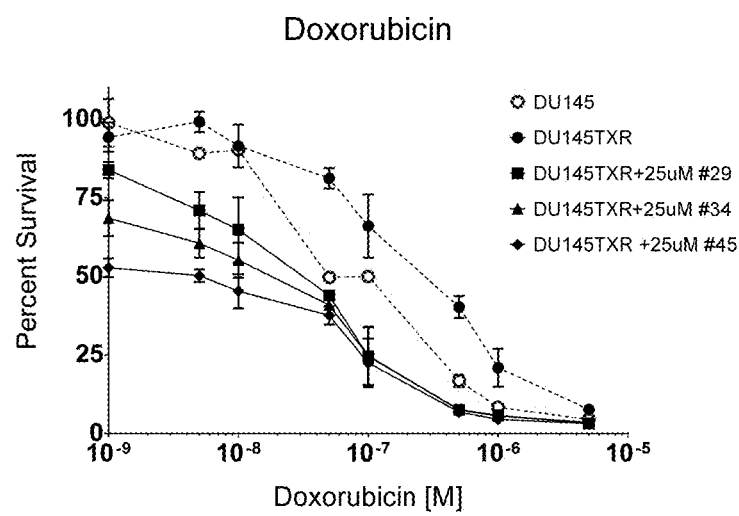

FIGS. 3A-3B are plots that show an example of the re-sensitization of a multidrug resistant prostate cancer cell line to two different chemotherapeutics using the prostate cancer derived cell line, DU145 and the multidrug-resistant variant, DU145-TxR. Addition of 25 µM compound 29, 34 or 45 restores chemotherapeutic sensitivity of MDR prostate cancer cell line DU145-TxR to that of nonresistant parental DU145. Cell viability was measured by the MTT (3-(4,5-dimethylthiazol-2-yl)-2,5-diphenyl tetrazolium bromide assay conducted as described previously. After 48 hours of treatment with Paclitaxel or Doxorubicin alone or in the presence of 25 µM compound 29, 34, or 45 media was removed and cells were washed twice with phosphate buffered saline (PBS) and MTT assay was conducted 24 hours later. Data expressed as mean±SEM.

Compound SMU-19 was found to not affect multidrug resistance in these cell culture studies and was not included in the FIG. Cell viability was measured by the MTT (3-(4, 5-dimethylthiazol-2-yl)-2,5-diphenyl tetrazolium bromide assay conducted as described previously (36).

FIGS. 3A-3B clearly demonstrate that compounds SMU-29, SMU-34 and SMU-45 reverse the Paclitaxel resistance phenotype of the DU145TxR to drug sensitivity levels that are equivalent to the non-drug resistant DU145 parent cell lines (left panels). Studies testing the re-sensitization of the drug resistant cells to a different chemotherapeutic, doxorubicin (right panels), suggest that the reversal of Paclitaxel resistance reflects a general reversal of multidrug resistance, since doxorubicin resistance by DU145TxR is also reversed to levels equivalent to the non-resistant DU145 parental strain.

Hyper-sensitization of cancers to chemotherapeutics. Other studies (not shown) using the ovarian cancer cell lines A2780 indicated that the presence of compounds SMU-29, SMU-34 or SMU-45 hyper-sensitized the cells to doxorubicin. The sensitivity of normal, not chemotherapy resistant A2780 ovarian cancer cell lines to doxorubicin was increased by several orders of magnitude in these assays.

Toxicity analysis. Toxicity studies using non-cancerous cells suggested low overall toxicity of the compounds by themselves at the same concentrations of compounds where reversal of chemotherapy resistance or hyper-sensitization of ovarian cancer cell lines was observed (not shown).

Cell Culture Assays.

Figure 4A:
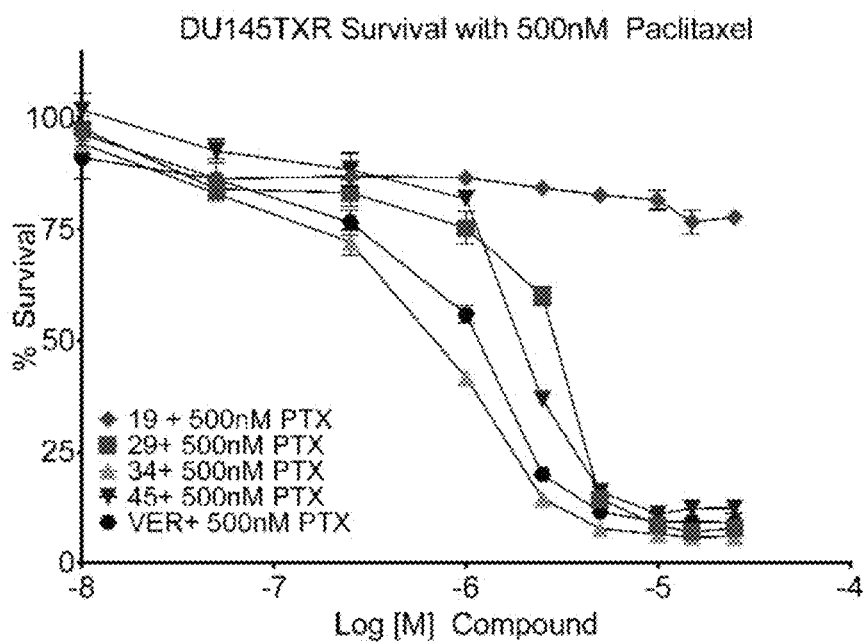
FIGS. 4A and 4B are graphs that show the in silico identified P-gp inhibitors potentiate the cytotoxic effects of paclitaxel in the MDR human prostate cancer cell line DU145TxR. Cells were incubated with 50 nM-25 μM inhibitor 19 (diamonds), 29 (squares), 34 (triangles), 45 (inverted-triangles), or verapamil (octagons) with 500 nM paclitaxel (top) or without paclitaxel (bottom) for 48 hours and survival was determined by MTT assay as previously described. Values represent the mean±SEM of at least two separate experiments performed in triplicate.
Figure 4B:
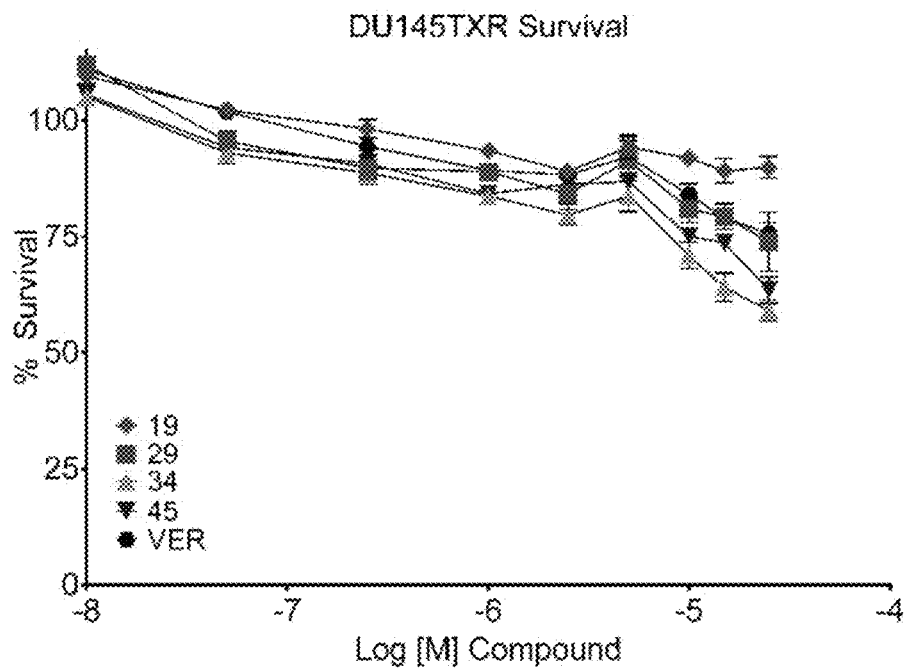

FIGS. 4A and 4B show the in silico identified P-gp inhibitors potentiate the cytotoxic effects of paclitaxel in the MDR human prostate cancer cell line DU145TxR. Cells were incubated with 50 nM-25 µM inhibitor 19 (diamonds), 29 (squares), 34 (triangles), 45 (inverted-triangles), or verapamil (octagons) with 500 nM paclitaxel (top) or without paclitaxel (bottom) for 48 hours and survival was determined by MTT assay as previously described. Values represent the mean±SEM of at least two separate experiments performed in triplicate.

A range of experimental inhibitor concentrations was added in the presence of 500 nM paclitaxel and the cell viability was assessed using the MTT assay. The results shown in FIG. 4A indicate that three of the four compounds, compounds 29 (squares), 34 (triangles) and 45 (inverted triangles) strongly affected the sensitivity of the resistant DU145TxR cells to paclitaxel at that concentration, similar to the effects of verapamil (octagons), a known resistance-modifying agent and competitive inhibitor of P-gp drug transport (Yusa and Tsuruo, 1989). Compound 19 (diamonds) had no effect on paclitaxel sensitivity of DU145TxR. To test whether the loss in cell viability may be caused by the compounds themselves, similar studies as above were performed in the absence of paclitaxel, FIG. 4B. The results clearly showed that the re-sensitization effect by compounds 29, 34 and 45 was likely not a result of intrinsic toxicity of P-gp inhibitors at tested concentrations, since 1 µM of inhibitors reduced survival by less than 20% in the absence of paclitaxel.

In order to compare the efficacy of inhibitors, the potentiation concentration of inhibitor resulting in 50% reduction in cell viability, $PC_{50}$, in the presence of 500 nM paclitaxel was calculated from the data in FIG. 4A. The $PC_{50}$ of compounds 29, 34, 45 were calculated to be 2.33±0.01 µM, 0.57±0.003 µM and 2.0±0.01 µM respectively, very similar to the known inhibitor, verapamil, with a $PC_{50}$ of 0.86±0.01 µM. The $PC_{50}$ for compound 19 was not determined, as it seemed to have no effect on the toxicity of paclitaxel in these experiments.

Figure 5A:
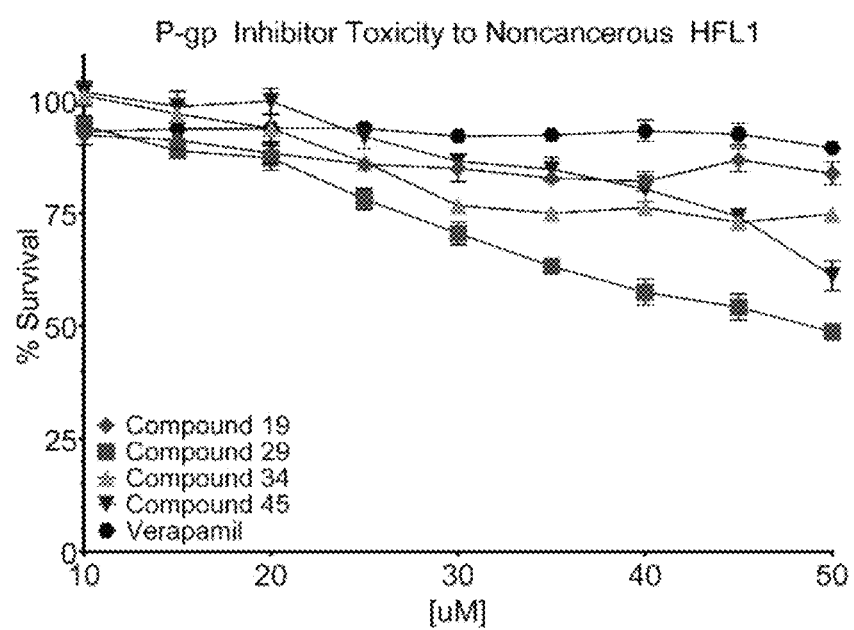
FIGS. 5A to 5C are graphs that show the intrinsic toxicities of experimental compounds: The effects of compounds 19 (diamonds), 29 (squares), 34 (triangles), 45 (inverted triangles) and verapamil (octagons) on the survival of (5A) noncancerous HFL1, (5B) prostate cancer cell line, DU145, (5C) MDR prostate cancer cell line, DU145TxR. Percent survival determined by MTT assay calculated relative to cells treated with equal volume DMSO vehicle and represent the mean±SEM from 2-4 separate experiments, each experiment performed in triplicate wells.
Figure 5B:
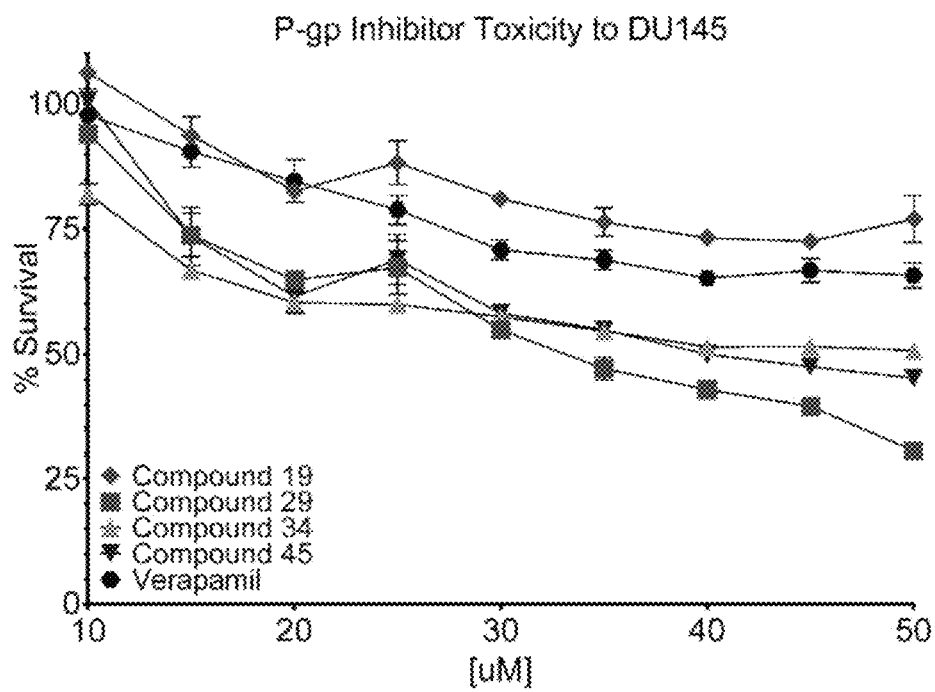
Figure 5C:
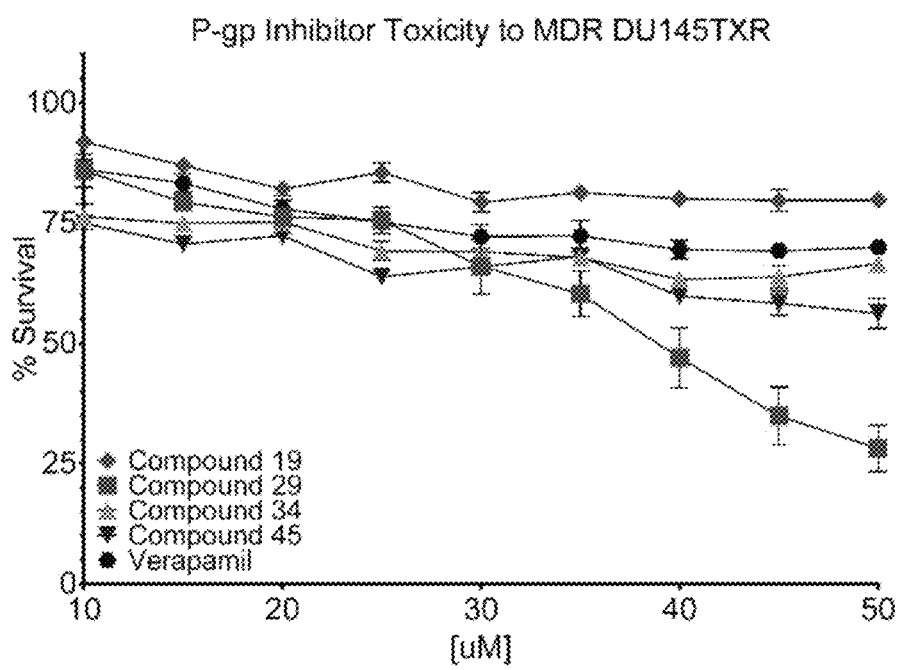

FIGS. 5A to 5C show the intrinsic toxicities of experimental compounds: The effects of compounds 19 (diamonds), 29 (squares), 34 (triangles), 45 (inverted triangles) and verapamil (octagons) on the survival of (5A) noncancerous HFL1, (5B) prostate cancer cell line, DU145, (5C) MDR prostate cancer cell line, DU145TxR. Percent survival determined by MTT assay calculated relative to cells treated with equal volume DMSO vehicle and represent the mean±SEM from 2-4 separate studies, each study performed in triplicate wells.

The intrinsic in vitro toxicities of identified compounds were evaluated to determine their potential therapeutic window. This was assessed in a noncancerous cell line (HFL1) and the human prostate cancer cell lines DU145 and the MDR sub-line DU145TxR. The potential toxicity of the compounds were assessed at concentrations that centered around 25 µM. At this concentration the compounds were shown to significantly inhibit ATP hydrolysis in biochemical assays with purified P-gp (Brewer et al., 2014). The presence of 25 µM of compounds 29, 34 and 45 also caused close to full re-sensitization of the multidrug resistant DU145TxR cells to paclitaxel as shown in FIG. 5C. In vitro cytotoxic concentrations determined using the HFL1 cell line have been shown to be comparable to whole animal toxicity testing as predictors of human toxicity (Barile and Cardona, 1998; Yang et al., 2002). The three cell lines, HFL1, DU145 and DU145TxR were exposed to verapamil (octagons), compound 19 (diamonds), 29 (squares), 34 (triangles) and 45 (inverted triangles) for 48 hours and survival was determined using the MTT assay. The $IC_{50}$ values are summarized in Table 1 and were calculated from graphs shown in FIG. 2A-C.

TABLE 1

$IC_{50}$ (µM) concentration for P-gp inhibitors ± standard error. Values were calculated from the mean of 2-4 separate experiments performed in triplicate wells.
$IC_{50}$ (µM) concentration for P-gp inhibitors ± standard error. Values were calculated from the mean of 2-4 separate experiments performed in triplicate wells.

| $IC_{50}$ (µM) | SMU-19 | SMU-29 | SMU-34 | SMU-45 | Verapamil |
|---|---|---|---|---|---|
| HFL1 | 780.3 ± 0.37 | 48.2 ± 0.01 | 85.2 ± 0.04 | 60.3 ± 0.02 | ND |
| DU145 | 106.3 ± 0.10 | 33.4 ± 0.01 | 47.2 ± 0.02 | 41.2 ± 0.03 | 74.5 ± 0.04 |
| DU145TxR | ND | 37.9 ± 0.02 | 200.3 ± 0.17 | 99.3 ± 0.08 | 147.5 ± 0.10 |

ND, not determined ND, not determined.

Figure 6A:
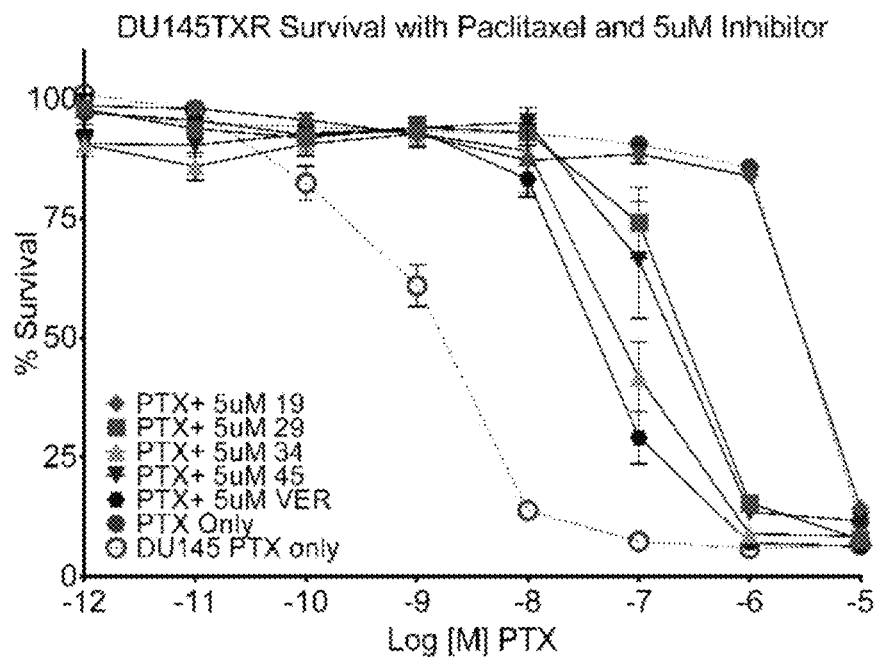
FIGS. 6A to 6C are graphs that show dose dependent sensitization of MDR prostate cancer cell line DU145TxR. DU145TxR cells (closed symbols) were incubated with various concentrations of paclitaxel and 5 μM (6A), 10 μM (6B), or 25 μM (6C) in silico identified P-gp inhibitors 19 (diamonds), 29 (squares), 34 (triangles), 45 (inverted triangles) and verapamil (octagons). For reference, the DU145TxR (closed circle) and DU145 (open circle) incubated with paclitaxel only are also included. Values are mean±SEM from at least 2 separate experiments performed in triplicate wells. The data were normalized to the intrinsic toxicities as determined in experiments from FIG. 5 of each of the compounds for each of the corresponding concentrations.
Figure 6B:
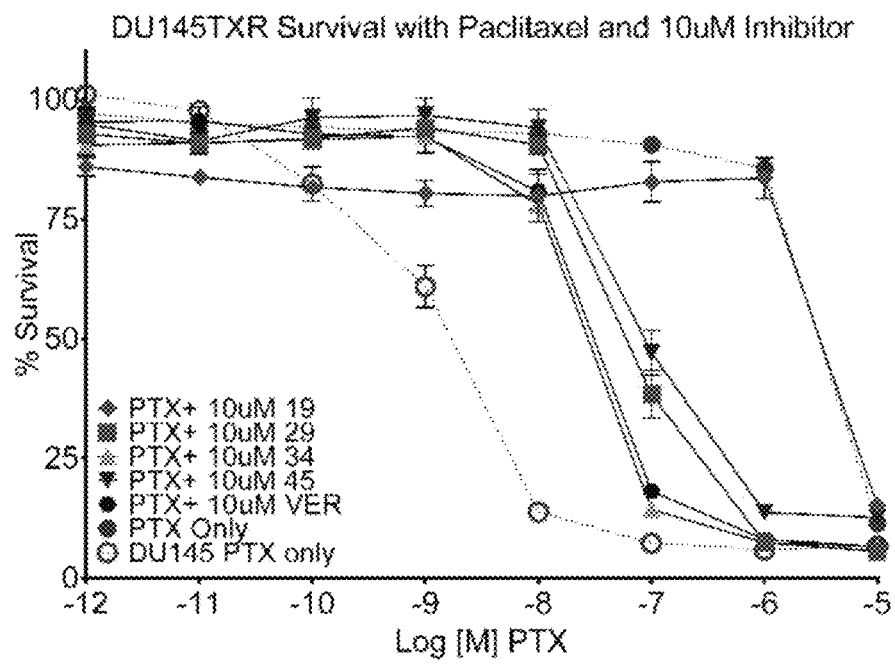
Figure 6C:
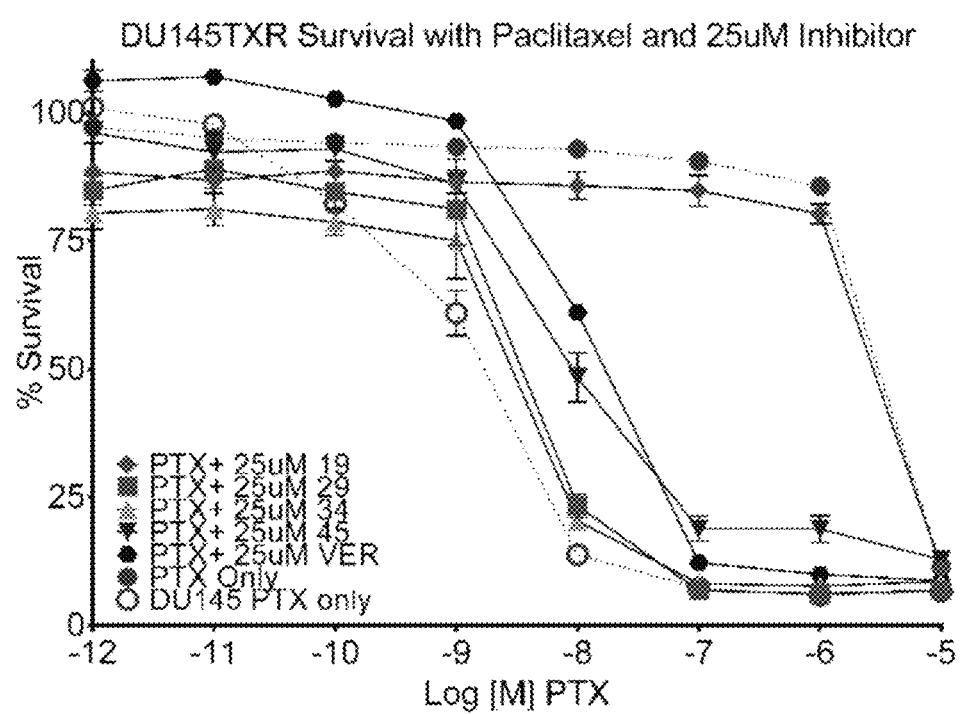

FIGS. 6A to 6C show the dose dependent sensitization of MDR prostate cancer cell line DU145TxR. DU145TxR cells (closed symbols) were incubated with various concentrations of paclitaxel and 5 µM (FIG. 6A), 10 µM (FIG. 6B), or 25 µM (FIG. 6C) in silico identified P-gp inhibitors 19 (diamonds), 29 (squares), 34 (triangles), 45 (inverted triangles) and verapamil (octagons). For reference, the DU145TxR (closed circle) and DU145 (open circle) incubated with paclitaxel only are also included. Values are mean±SEM from at least 2 separate experiments performed in triplicate wells. The data were normalized to the intrinsic toxicities as determined in studies from FIGS. 5A to 5C of each of the compounds for each of the corresponding concentrations.

Dose Dependent Sensitization of MDR Prostate Cancer Cell Line: To determine the degree to which the MDR prostate cancer cell line DU145TxR could be sensitized to paclitaxel the inventors determined cell survival at increasing concentrations of paclitaxel in the presence of three concentrations of P-gp inhibitors. FIGS. 6A, 6B and 6C show the survival of DU145TxR at increasing concentration of paclitaxel in the presence of 5 µM, 10 µM and 25 µM of the experimental compounds, respectively. The open circles represent the parental DU145 cell line in the presence of paclitaxel without addition of any inhibitor compound. The closed circles represent the survival of the multidrug resistant DU145TxR in the presence of paclitaxel alone. Diamonds represent the presence of compound 19, squares represent the presence of compound 29, triangles represent compound 34, inverted triangles compound 45 and octagons represent the presence of verapamil. The data indicate that increased sensitization of DU145TxR is already observed in the presence of 5 µM of the experimental compounds, 29, 34 and 45. At that concentration over 10-fold increase in paclitaxel sensitivity in DU145TxR is observed compared to DU145TxR without P-gp inhibitors. Doubling the concentration of the compounds to 10 µM approximately doubled the DU145TxR sensitivity to paclitaxel. At both concentrations (5 µM and 10 µM) the effects of the compounds were comparable to those of the known MDR modulator, verapamil, while compound 19 showed no effect on cell viability. At 25 µM concentration, compounds 29 and 34 sensitized the multidrug resistant DU145TxR to $IC_{50}$ values that were close to those observed for the parental, sensitive DU145 cell line (open circles), an 800- or 1200-fold sensitization, respectively. Sensitization of DU145TxR to paclitaxel by the compounds 29 (squares), 34 (triangles) and 45 (inverted triangles) exceeded sensitization by verapamil (octagons). Compound 19 did not show any effect on cell viability in any of the studies at any concentration (diamonds).

Extended biophysical evaluations by the present inventors are provided in their article "In Silico Screening for Inhibitors of P-Glycoprotein That Target the Nucleotide Binding Domains" (Brewer et al., 2014), Mol Pharmacol 86:716-726, December 2014, the entirety of which is incorporated herein by reference. Brewer et al., in FIGS. 4 and 5, provide additional information about the mechanism of inhibitor action that was predicted computationally was confirmed using electron spin resonance spectroscopy (ESR) and titration of accessible nucleotide binding sites. Inhibitors 19, 34 and 45 were predicted to interact directly with the nucleotide binding sites (FIG. 5 of Brewer). The ESR studies of Brewer et al., show that these three compounds interfere directly with the nucleotide binding sites in as they reduce the number of binding sites that are able to bind an ATP analog, see FIGS. 4C, 4E and 4F of Brewer (incorporated herein by reference). Compound 29 was predicted computationally to bind outside of the nucleotide bindings sites (FIG. 5 of Brewer) and was shown to not interfere with ATP binding in ESR experiments, see FIG. 4D of Brewer.

Figure 7:
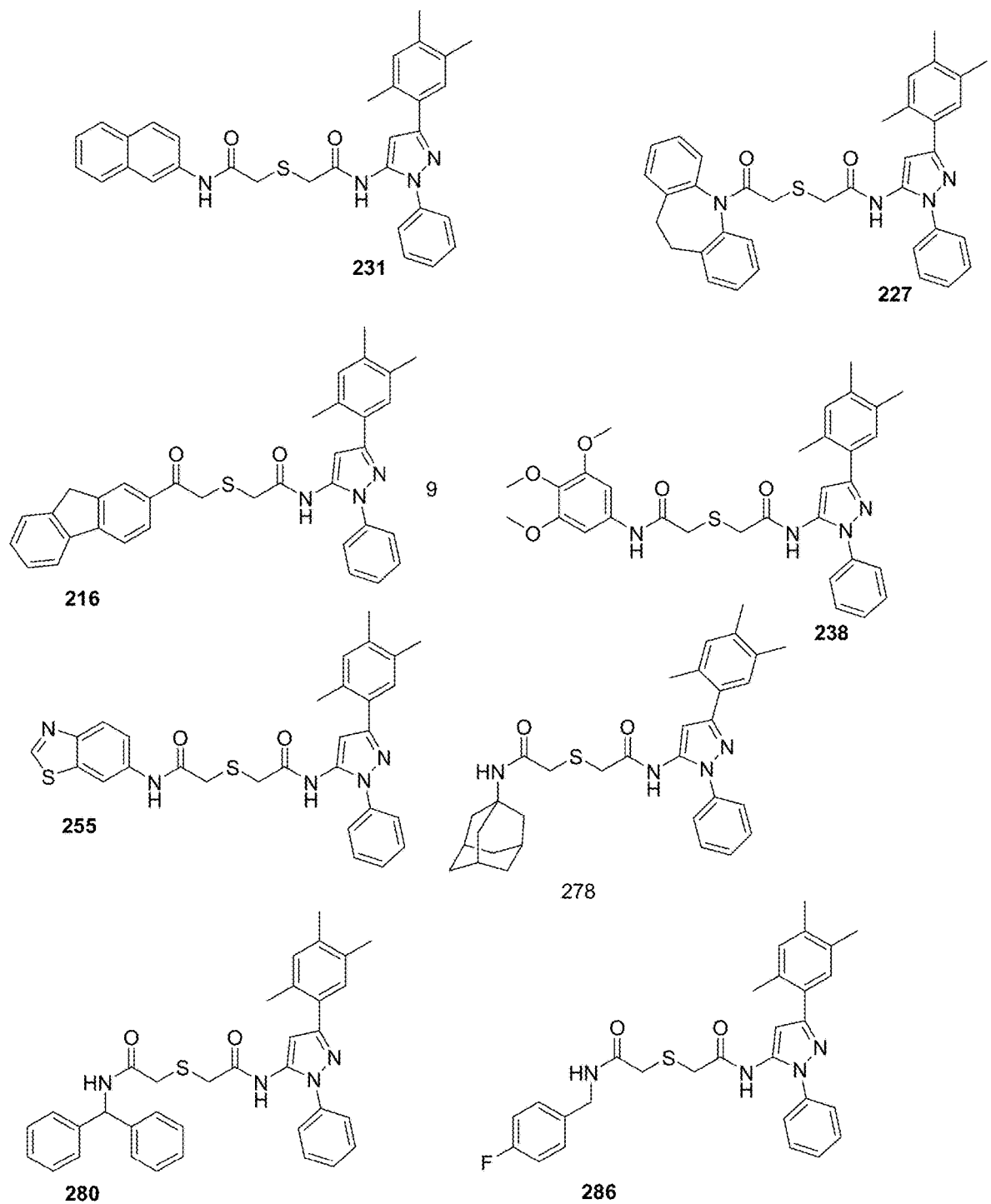
FIG. 7 shows chemical structures of SMU 29-variants with improved characteristics.
Figure 8:
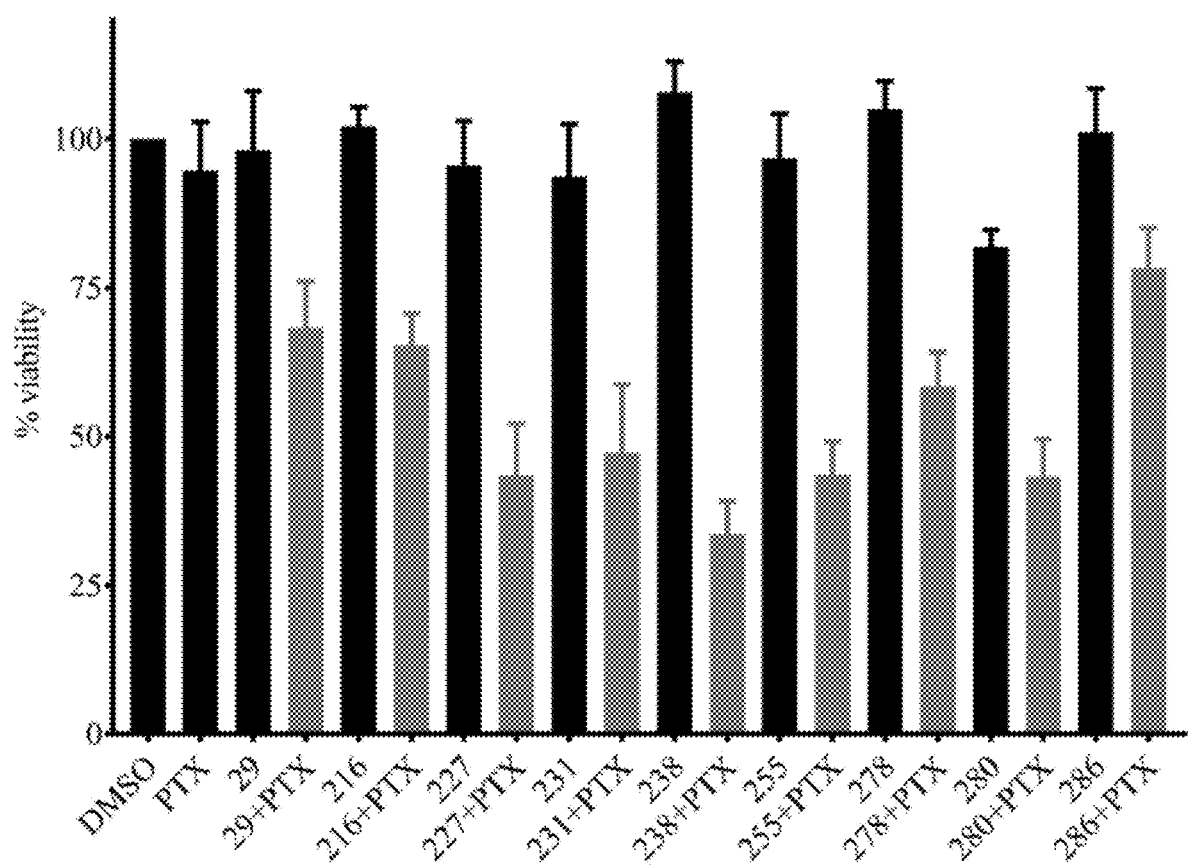
FIG. 8 is a bar graph showing one example of the utility of the compounds in re-sensitizing highly chemotherapy-resistant prostate cancer cells to the chemotherapeutic paclitaxel.

Variants of SMU 29 with improved characteristics were synthesized. See FIG. 7. IUPAC names:

SMU 29-216:
2-((2-(9H-fluoren-2-yl)-2-oxoethyl)thio)-N-(1-phenyl-3-(2,4,5-trimethylphenyl)-1H-pyrazol-5-yl)acetamide SMU 29-227:
2-((2-(10,11-dihydro-5H-dibenzo[b,f]azepin-5-yl)-2-oxoethyl)thio)-N-(1-phenyl-3-(2,4,5-trimethylphenyl)-1H-pyrazol-5-yl)acetamide SMU 29-231:
N-(naphthalen-2-yl)-2-((2-oxo-2-((1-phenyl-3-(2,4,5-trimethylphenyl)-1H-pyrazol-5-yl)amino)ethyl)thio)acetamide SMU 29-238:
2-((2-oxo-2-((1-phenyl-3-(2,4,5-trimethylphenyl)-1H-pyrazol-5-yl)amino)ethyl)thio)-N-(3,4,5-trimethoxyphenyl)acetamide SMU 29-255:
N-(benzo[d]thiazol-6-yl)-2-((2-oxo-2-((1-phenyl-3-(2,4,5-trimethylphenyl)-1H-pyrazol-5-yl)amino)ethyl)thio)acetamide SMU 29-278:
N-((3s,5s,7s)-adamantan-1-yl)-2-((2-oxo-2-((1-phenyl-3-(2,4,5-trimethylphenyl)-1H-pyrazol-5-yl)amino)ethyl)thio)acetamide SMU 29-280:
N-benzhydryl-2-((2-oxo-2-((1-phenyl-3-(2,4,5-trimethylphenyl)-1H-pyrazol-5-yl)amino)ethyl)thio)acetamide SMU 29-286:
N-(4-fluorobenzyl)-2-((2-oxo-2-((1-phenyl-3-(2,4,5-trimethylphenyl)-1H-pyrazol-5-yl)amino)ethyl)thio)acetamide FIG. 8 shows the effects on cell viability after treatment of a multidrug-resistant prostate cancer cell line, DU145TXR$^I$, with either chemotherapeutic alone (PTX), solvent alone (DMSO), 29 or 29 variants alone (black bars), or in combination of 29 or 29 variants and paclitaxel (grey bars). The concentration of paclitaxel was 100 nM, the concentration of experimental compounds was 5 µM. The cells were seeded in 96 well plates and treated for 48 hours with the respective compounds. Cell viability was determined using an MTT assay.

The present inventors have successfully identified a number of lead compounds that inhibit the power-stroke of drug expulsion catalyzed by the multidrug resistance P-glycoprotein. These results show that effective inhibition of P-glycoprotein can occur by targeting the nucleotide binding domains of the protein that can cause re-sensitization of multidrug resistant cancer cell lines. Through biophysical assays the inventors determined additional non-limiting information about the mechanism of P-glycoprotein inhibition by the identified compounds. The identified P-glycoprotein inhibitor lead compounds are specific inhibitors that can be co-administered with traditional chemotherapeutics to treat chemotherapy resistant cancers or multidrug resistant infections. The identified P-glycoprotein inhibitor compounds sensitize cancer stem cells to chemotherapeutic treatment, removing these cells as a source of recurrent cancer. The identified P-glycoprotein inhibitor lead compounds are specific inhibitors that can be co-administered with therapeutics that do not normally penetrate the blood brain barrier. This increases the efficacy of drugs when access to the central nervous system by the drug is prohibited by P-glycoprotein.

Co-administration with chemotherapeutic and/or anti-cancer agents. In accordance with the methods of the invention, the compositions of the present invention can be co-administered in combination with anti-cancer agents ("anticancer agent" or "chemotherapeutic agent"). Without intending to be bound by any particular mechanism or effect, such co-administration can in some cases provide one or more of several unexpected benefits including: (i) co-administration of the compositions of the present invention and the chemotherapeutic agent has a synergistic effect on induction of cancer cell death; (ii) co-administration provides a better therapeutic result than administration of the chemotherapeutic agent alone, e.g., greater alleviation or amelioration of one or more symptoms of the cancer, diminishment of extent of disease, delay or slowing of disease progression, amelioration, palliation or stabilization of the disease state, partial or complete remission, prolonged survival or other beneficial therapeutic results; (iii) co-administration of the compositions of the present invention increases the sensitivity of cancer cells to the anticancer agent, allowing lower doses of the agent to be administered to the patient or allowing an agent to be used for treatment of cells otherwise resistant to the agent or otherwise refractory to treatment; and (iv) co-administration of the compositions of the present invention and the chemotherapeutic agent increases killing of cells in hypoxic regions of tumors that are not efficiently killed by the agent alone.

Examples of chemotherapeutic and/or anti-cancer agents include agents such as paclitaxel, doxorubicin, vincristine, vinblastine, vindesine, vinorelbin, taxotere (DOCETAXEL), topotecan, camptothecin, irinotecan hydrochloride (CAMPTOSAR), etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (ARA-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (ARA-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen, mustard, uracil mustard, pipobroman, 4-ipomeanol, dihydrolenperone, spiromustine, geldanamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluorometh-yl) propionanilide, Herceptin, anti-CD20 (Rituxan), interferon, alpha, interferon beta, interferon gamma, interleukin 2, interleukin 4, interleukin 12, tumor necrosis factors, and radiation.

The disclosed method is particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Another embodiment of the present invention is a method of treating a subject with a cancer that has become drug resistant. Optionally, the method of the invention can be used for a multi-drug resistant cancer. The method comprises the step of administering an effective amount of a compound of the present invention, pharmaceutically acceptable salt, solvate, clathrate, or a prodrug thereof. Preferably, one or more additional anti-cancer drugs are co-administered with a compound of the invention. Examples of anti-cancer drugs are described below. For example, the co-administered anti-cancer drug is an agent that stabilizes mictotubules, such as TAXOL or a taxanes derivative.

In another embodiment, a compound of the invention can be administered as adjuvant therapy to prevent the reoccurrence of cancer. For example, stage II and stage III melanoma are typically treated with surgery to remove the melanoma followed by chemotherapeutic treatment to prevent the reoccurrence of cancer. In one embodiment, one or more additional anti-cancer drugs are co-administered with a compound of the invention as adjuvant therapy. Examples of anti-cancer drugs are described herein. In one embodiment, the co-administered anti-cancer drug is an agent that stabilizes microtubules, such as TAXOL or a taxanes derivative. In another embodiment, the co-administered anti-cancer drug is an immunotherapeutic anticancer agent.

Drug resistant cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial Cancer, pancreatic cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendroglioma, meningioma, spinal cord tumors, melanoma, neuroblastoma, pheochromocytoma, Types 1-3 endocrine neoplasia, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease. Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562(chronic) cell line); neutrophilic leukemia; eosinophilic leukemia; monocytic leukemia (e.g., as exemplified by the THP-1(acute) cell line); myelomonocytic leukemia; Naegeli-type myeloid leukemia; and non-lymphocytic leukemia. Other examples of leukemias are described in Chapter 60 of The Chemotherapy Sourcebook, Michael C. Perry Ed., Williams & Williams (1992) and Section 36 of Holland Frie Cancer Medicine 5th Ed., Bast et al. Eds., B. C. Decker Inc. (2000). The entire teachings of the preceding references are incorporated herein by reference.

Additional drug resistant cancers that can be treated or prevented by the methods of the present invention include, but are not limited to oral cavity and pharynx cancers, including tongue, mouth, pharynx, and other oral cavity cancers; digestive system cancers, including esophagus, small intestine, rectum, anus, anal canal, anorectum, liver and intrahepatic bile duct, gallbladder and other biliary, pancreas and other digestive organs; respiratory system cancers, including larynx and bronchus; bone and joint cancers; soft tissue (including heart) cancers; genital system cancers, including uterine cervix, uterine corpus, ovary, vulva, vagina and other genital, female, testis, penis and other genital, male; urinary system cancers, including kidney and renal pelvis, and ureter and other urinary organs; eye and orbit cancers; leukemia, including acute myeloid leukemia and chronic myeloid leukemia.

Numerous non-cancer diseases that involve excessive or hyperproliferative cell growth, termed hyperplasia that have become drug resistant can be treated with the instant compositions. Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

The present disclosure provides a method of treating a subject having cells that are resistant to one or more drugs by identifying a subject having one or more drug resistant cells; administering to the subject a pharmaceutically effective amount of an inhibitor compound having one of the following structural formulas:

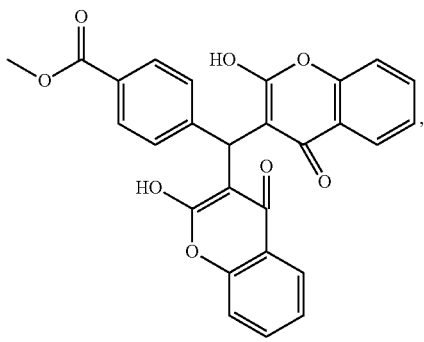

-continued

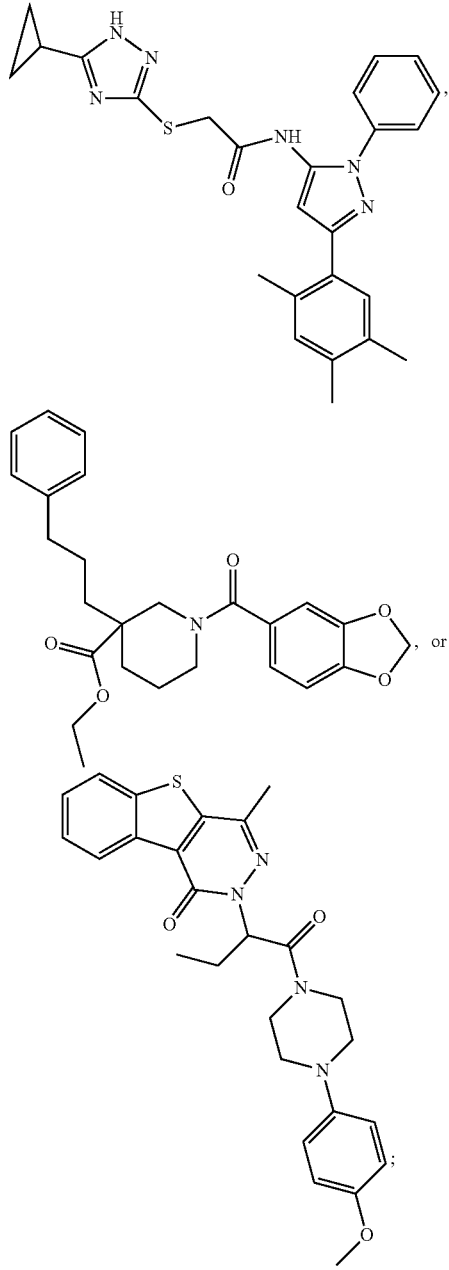

and contacting one or more drug resistant cells with the inhibitor compound to reduce the export of the inhibitor compound from the one or more drug resistant cells and to block the transport of chemotherapeutic drug(s) from the one or more drug resistant cancer cells.

The inhibitor compound interacts with an exporter protein. In one embodiment, the inhibitor compound interacts with drug-toxin pumping structures of a P-glycoprotein. In one embodiment, the inhibitor compound interacts with ATP binding domain(s) of a P-glycoprotein and the inhibitor compound does not bind to drug binding site(s) on the P-glycoprotein. In one embodiment, the inhibitor compound is a P-glycoprotein inhibitor. The inhibitor compound is minimally transported by a P-glycoprotein.

The one or more drug resistant cancer cells may be one or more multidrug resistant tumor cells, cancer cells, cancer stem cells, bacterial cells, virus infected cells and the like.

The method may further include the step of administering one or more chemotherapeutic agents to the subject before further treatment, during treatment or after treatment with the inhibitor compound.

The inhibitor compound is effective for increasing the effectiveness of the chemotherapeutic drug or antibiotic agents to inhibit proliferation, inducing cell death, or indirectly inhibiting development of a tumor by suppressing tumor angiogenesis.

The inhibitor compound also is effective for increasing an efficacy of one or more chemotherapeutics or antibiotic agents and/or decreasing toxicity of the chemotherapeutic treatment(s) or antibiotic treatments.

The present invention encompasses all compounds having identical molecular formula but differing in the nature or sequence of bonding of their atoms or in the arrangement of their atoms in space. A carbon atom bonded to four non-identical substituents is termed a "chiral center" and a compound with one chiral center has two enantiomeric forms of opposite chirality. It is contemplated that any embodiment discussed in this specification includes compositions having one or more centers of chirality and exist as stereochemically isomeric forms. The present invention encompasses all isomers of the compositions disclosed herein. As used herein "isomers" denote differ arrangements of atoms in space and include "stereoisomers". Stereoisomers that are not mirror images of one another are termed "diastereomers" and stereoisomers that are nonsuperimposable mirror images are termed "enantiomers" or sometimes "optical isomers." The present invention encompasses all variations at each of these chiral centers to include numerous composition having the same formula but different arrangement of their atoms in space.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Barile, F. A., and Cardona, M. (1998). Acute cytotoxicity testing with cultured human lung and dermal cells. In vitro cellular & developmental biology Animal 34, 631-635.

Berridge, M. V., and Tan, A. S. (1993) Characterization of the cellular reduction of 3-(4,5-dimethylthiazol-2-yl)-2,5-diphenyltetrazolium bromide (MTT): subcellular localization, substrate dependence, and involvement of mitochondrial electron transport in MTT reduction, *Arch Biochem Biophys* 303, 474-482.

Brewer, F. K., Follit, C. A., Vogel, P. D., and Wise, J. G. (2014). In silico Screening for Inhibitors of P-Glycoprotein that Target the Nucleotide Binding Domains. Molecular pharmacology 86, 716-726.

Kupcsik, L. (2011) Estimation of cell number based on metabolic activity: the MTT reduction assay, *Methods Mol Biol* 740, 13-19.

Takeda, M., Mizokami, A., Mamiya, K., Li, Y. Q., Zhang, J., Keller, E. T., and Namiki, M. (2007) The establishment of two paclitaxel-resistant prostate cancer cell lines and the mechanisms of paclitaxel resistance with two cell lines, *Prostate* 67, 955-967.

van Meerloo, J., Kaspers, G. J., and Cloos, J. (2011) Cell sensitivity assays: the MTT assay, *Methods Mol Biol* 731, 237-245.

Yang, A., Cardona, D. L., and Barile, F. A. (2002). Subacute cytotoxicity testing with cultured human lung cells. Toxicology in vitro: an international journal published in association with BIBRA 16, 33-39.

Yusa, K., and Tsuruo, T. (1989). Reversal mechanism of multidrug resistance by verapamil: direct binding of verapamil to P-glycoprotein on specific sites and transport of verapamil outward across the plasma membrane of K562/ADM cells. Cancer Res 49, 5002-5006.

What is claimed is:

1. A method of sensitization and re-sensitization of a prostate or liver cancer cells to a chemotherapeutic comprising the steps of:
   identifying a subject having one or more cancer cells that express P-glycoprotein in need of sensitization and re-sensitization to one or more chemotherapeutic;
   administering to the subject a pharmaceutically effective amount of an inhibitor compound having one of the following structural formulas:

231

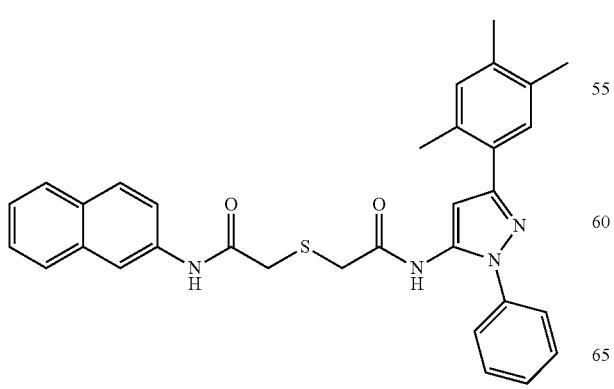

227

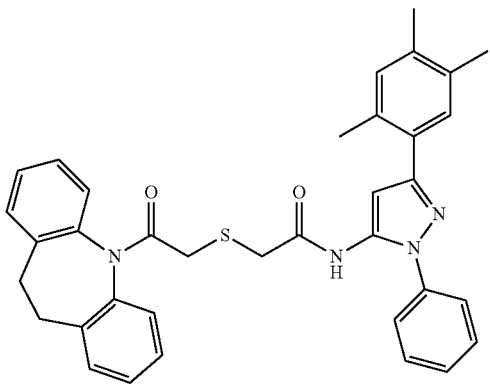

216

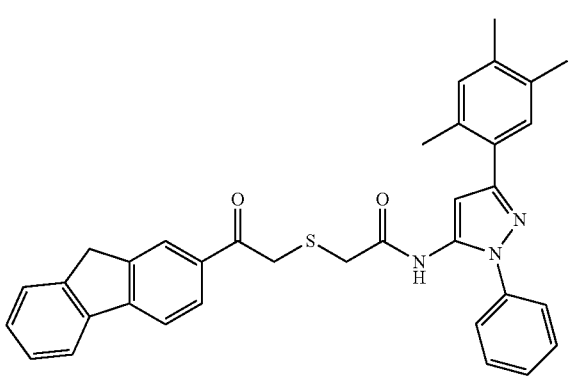

238

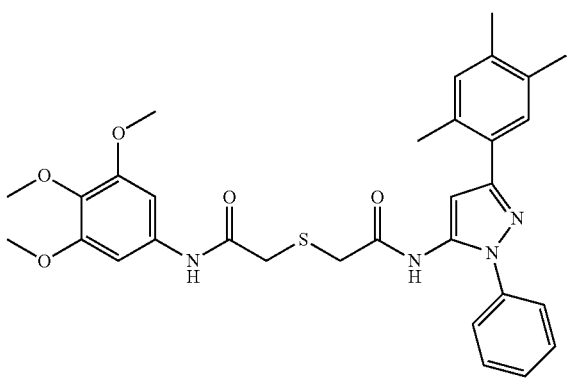

255

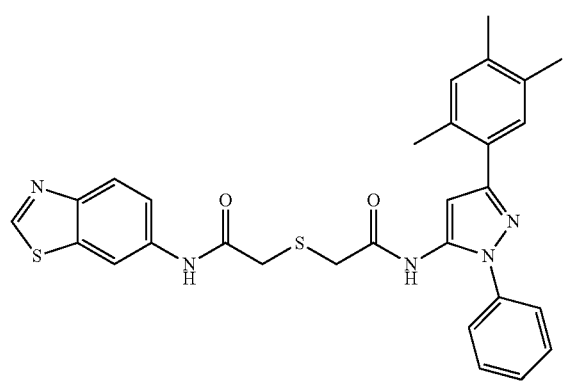

278

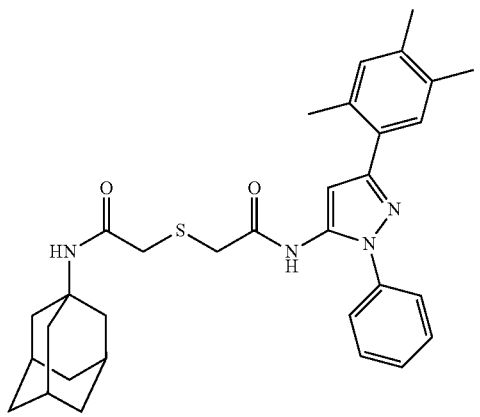

280

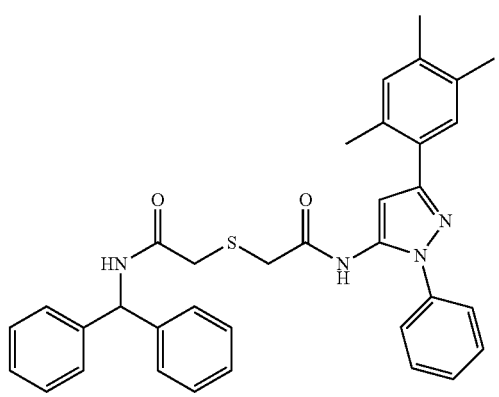

286

2. The method of claim 1, wherein the inhibitor compound interacts with one or more ATP binding domain(s) of a P-glycoprotein, or does not bind to drug binding sites on the P-glycoprotein.

3. The method of claim 1, wherein the prostate or liver cancer cells are multidrug resistant cancer cells or tumor cells or cancer stem cells.

4. The method of claim 1, further comprising the step of administering one or more chemotherapeutic agents to the subject.

* * * * *